(12) United States Patent
Cunningham et al.

(10) Patent No.: US 7,961,315 B2
(45) Date of Patent: *Jun. 14, 2011

(54) FLUORESCENCE DETECTION ENHANCEMENT USING PHOTONIC CRYSTAL EXTRACTION

(75) Inventors: Brian T. Cunningham, Champaign, IL (US); Nikhil Ganesh, Champaign, IL (US); Patrick C. Mathias, Orlando, FL (US); Ian D. Block, Champaign, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/802,890

(22) Filed: Jun. 15, 2010

(65) Prior Publication Data

US 2011/0031409 A1   Feb. 10, 2011

Related U.S. Application Data

(63) Continuation of application No. 11/986,156, filed on Nov. 19, 2007, now Pat. No. 7,768,640.

(60) Provisional application No. 60/916,462, filed on May 7, 2007.

(51) Int. Cl.
*G01J 3/30* (2006.01)

(52) U.S. Cl. .......... 356/317; 356/72; 356/364; 356/326; 356/417; 422/82.07

(58) Field of Classification Search .................. 356/317, 356/72; 422/82.07; 359/368
See application file for complete search history.

(56) References Cited

U.S. PATENT DOCUMENTS

| | | | |
|---|---|---|---|
| 5,216,680 A | 6/1993 | Magnusson et al. | 372/20 |
| 6,078,705 A | 6/2000 | Neuschafer et al. | 385/12 |
| 6,289,144 B1 | 9/2001 | Neuschafer et al. | 385/12 |
| 6,707,561 B1 | 3/2004 | Budach et al. | 356/521 |
| 6,771,376 B2 | 8/2004 | Budach et al. | 356/521 |
| 6,867,869 B2 | 3/2005 | Budach et al. | 356/521 |
| 6,870,630 B2 | 3/2005 | Budach et al. | 356/521 |
| 6,990,259 B2 | 1/2006 | Cunningham | 385/12 |
| 7,023,544 B2 | 4/2006 | Cunningham et al. | |
| 7,064,844 B2 | 6/2006 | Budach et al. | 356/521 |
| 7,094,595 B2 | 8/2006 | Cunningham et al. | 435/287.2 |

(Continued)

FOREIGN PATENT DOCUMENTS

WO   WO 2007/129074   11/2007

OTHER PUBLICATIONS

International Preliminary Report on Patentability mailed Nov. 19, 2009 in PCT/US2007/024234, filed Nov. 19, 2007.

(Continued)

*Primary Examiner* — L. G Lauchman
(74) *Attorney, Agent, or Firm* — McDonnell Boehnen Hulbert & Berghoff LLP

(57) ABSTRACT

Enhancement of fluorescence emission from fluorophores bound to a sample and present on the surface of two-dimensional photonic crystals is described. The enhancement of fluorescence is achieved by the combination of high intensity near-fields and strong coherent scattering effects, attributed to leaky photonic crystal eigenmodes (resonance modes). The photonic crystal simultaneously exhibits resonance modes which overlap both the absorption and emission wavelengths of the fluorophore. A significant enhancement in fluorescence intensity from the fluorophores on the photonic crystal surface is demonstrated.

23 Claims, 9 Drawing Sheets

U.S. PATENT DOCUMENTS

| | | | |
|---|---|---|---|
| 7,118,710 B2 | 10/2006 | Cunningham | 422/82.09 |
| 7,167,615 B1 | 1/2007 | Wawro et al. | |
| 7,292,336 B2 * | 11/2007 | Cunningham et al. | 356/326 |
| 7,400,399 B2 | 7/2008 | Wawro et al. | 356/328 |
| 7,790,406 B2 * | 9/2010 | Cunningham et al. | 435/7.2 |
| 2002/0127565 A1 | 9/2002 | Cunningham et al. | 435/6 |
| 2003/0027327 A1 | 2/2003 | Cunningham et al. | 435/287.2 |
| 2003/0032039 A1 | 2/2003 | Cunningham et al. | 435/6 |
| 2003/0059855 A1 | 3/2003 | Cunningham et al. | 435/7.9 |
| 2007/0009380 A1 | 1/2007 | Cunningham | 422/58 |
| 2007/0009968 A1 | 1/2007 | Cunningham et al. | 435/7.9 |

OTHER PUBLICATIONS

Wawro et al., *Optical Fiber Endface Biosensor Based on Resonances in Dielectric Waveguide Gratings*, International Biomedical Optics Symposium Jan. 2000, Proceedings SPIE, vol. 3911, pp. 86-94 (2000).

International Search Report and Written Opinion mailed Nov. 13, 2008 in PCT/US2007/024234.

Zhang et al., "Solid-state fluorescence enhancement of organic dyes by photonic crystals", Journal of Materials Chemistry, vol. 17, No. 1, pp. 90-94 (2007).

Mathias et al., "Combined enhanced fluorescence and label-free biomolecular detection with a photonic crystal surface", Applied Optics, Optical Society of America, vol. 46, No. 12, pp. 2351-2360 (2007).

Moharam et al., "Rigorous coupled-wave analysis of planar-grating diffraction", Journal of Optical Society of America, vol. 71, No. 7, pp. 811-818 (1981).

Astratov et al., "Resonant Coupling of Near-Infrared Radiation to Photonic Band Structure Waveguides", Journal of Lightwave Technology IEEE, vol. 17, No. 11pp. 2050-2057 (1999).

Ganesh et al., "Photonic Crystal Enhanced Fluorescence", 2007 Conference on Lasers and Electro-Optics IEEE Piscataway, NJ, pp. 1133-1134 (2007).

Ganesh et al., "Enhanced fluorescence emission from quantum dots on a photonic crystal surface", Nature Nanotechnology, Nature Publishing Group, vol. 2, No. 8, pp. 515-520 (2007).

Jenison et al., *Interference-based detection of nucleic acid targets on optically coated silicon*, Nature Biotechnology vol. 19, pp. 62-65 (2001).

Cunningham et al., *Colorimetric Resonant Reflection as a Direct Biochemical Assay Technique*, Sensors and Actuators B, 4120, pp. 1-13 (2001).

Li et al., *A new method for label-free imaging of biomolecular interactions*, Sensors and Actuators B, vol. 99, pp. 6-13 (2004).

Cunningham et al., *A Plastic Colorimetric Resonant Optical Biosensor for Multi-parallel Detection of Label Free Biochemical Interactions*, Sensors and Actuators B, vol. 85, pp. 1-8 (2002).

Boonruang et al., *Multiline two-dimensional guided-mode resonant filters*, Applied Optics, vol. 45, No. 22, pp. 5740-5747 (2006).

Suh et al., *All-pass transmission or flattop reflection filters using a single photonic crystal slab*, Ameriacan Institute of Physics, Applied Physics Letters, vol. 84, No. 24, pp. 4905-4907 (2004).

Rosenberg et al., *Guided resonances in asymmetrical GaN photonic crystal labs observed in the visible spectrum*, Optics Express, vol. 13, No. 17, pp. 6564-6571 (2005).

Fan et al., *Analysis of guided resonances in photonic crystal slabs*, The American Physical Society, Physical Review Rev. B, vol. 65, pp. 235112-1-235112-8 (2002).

Astratov et al., *Resonant Coupling of Near-Infrared Radiation to Photonic Band Structure Waveguides*, Journal of Lightwave Technolology, vol. 17 No. 11, pp. 20502057 (1999).

Boroditsky et al., *Light extraction from optically pumped light-emitting diode by thin-slab photonic crystals*, American Institute of Physics, Applied Physics Letters, vol. 75, No. 6, pp. 1036-1038 (1999).

Boroditsky et al., *Spontaneous Emission Extraction and Purcell Enhancement from Thin-Film 2-D Photonic Crystals*, Journal of Lightwave Technology, vol. 17, No. 11, pp. 2096-2112 (1999).

Erchak et al., *Enhanced coupling to vertical radiation using a two-dimensional photinic crystal in a semiconductor light-emitting diode*, American Institute of Physics, Applied Physics Letters, vol. 78, No. 5, pp. 563-565 (2001).

Kobayashi et al., *Surface laser emission from solid polymer dye in a guided mode resonant grating filter structure*, American Institute of Physics, Applied Physics Letters, vol. 87, pp. 1511061-2 (2005).

Rosenblatt et al., *Resonant grating waveguide structures*, IEEE Journal of Quantum Electronics, vol. 33, No. 11, pp. 2038-2059 (1997).

Ganesh et al, *Near ultraviolet-wavelength photonic-crystal biosensor with enhanced surface-to-bulk sensitivity ratio*, American Institute of Physics, Applied Physics Letters, vol. 89, 023901 (2006).

Moharam et al., *Rigorous coupled-wave analysis of planar-grating diffraction*, Optical Society of America, vol. 71, No. 7, pp. 811-818 (1981).

Ding et al., *Use of nondegenerate resonant leaky modes to fashion diverse optical spectra*, Optics Express, vol. 12, No. 9, pp. 1885-1891 (2004).

Ichikawa et al., *Efficiency enhancement in a light-emitting diode with a two-dimensional surface grating photonic crystal*, American Institute of Physics, vol. 84, No. 4, pp. 457-459 (2004).

* cited by examiner

Fig. 6A   Θ = 11.2°
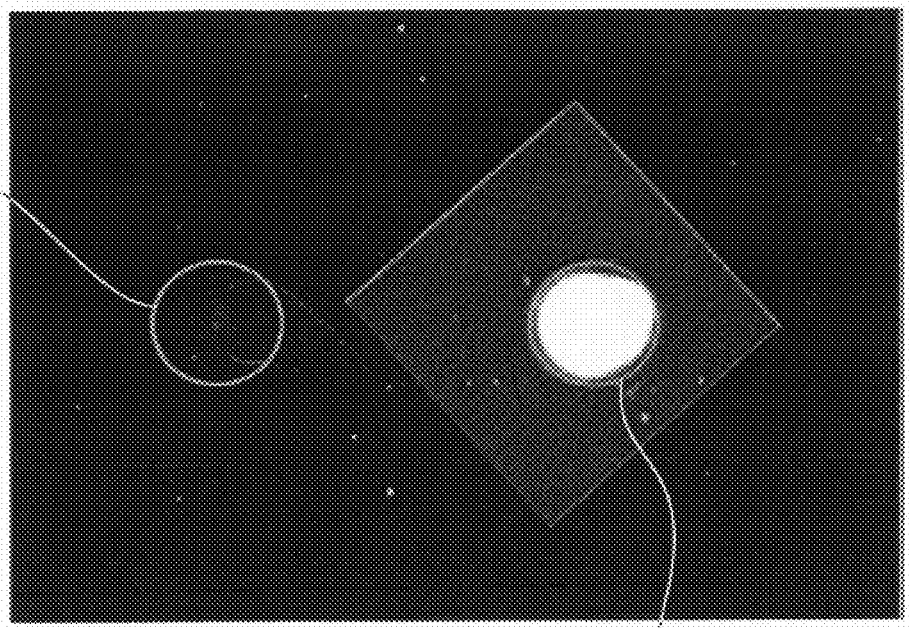
Fig. 6B   Θ = 0°
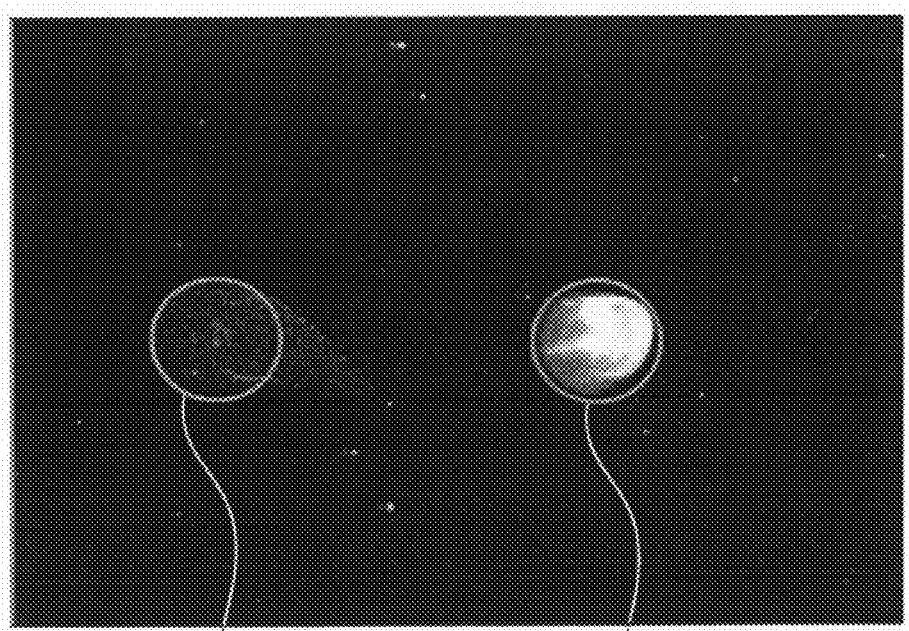

FLUORESCENCE DETECTION ENHANCEMENT USING PHOTONIC CRYSTAL EXTRACTION

CROSS-REFERENCE TO RELATED APPLICATIONS

This is a continuation of U.S. application Ser. No. 11/986,156 filed Nov. 19, 2007, which claims priority under 35 U.S.C. §119(e) to U.S. Provisional Application Ser. No. 60/916,462 filed May 7, 2007, the content of which is incorporated by reference herein.

STATEMENT REGARDING FEDERALLY SPONSORED RESEARCH OR DEVELOPMENT

This invention was made, at least in part, with United States governmental support awarded by the National Science Foundation under NSF BES 0427657. The United States Government has certain rights in this invention.

BACKGROUND OF THE INVENTION

Photonic crystals, also commonly referred to as photonic bandgap structures, are periodic dielectric structures exhibiting a spatially periodic variation in refractive index that forbids propagation of certain frequencies of incident electromagnetic radiation. The photonic band gap of a photonic crystal refers to the range of frequencies of electromagnetic radiation for which propagation through the structure is prevented in particular directions. A photonic crystal structure may be designed to exhibit extraordinarily high reflection efficiency at particular wavelengths, at which optical standing waves develop and resonate within the photonic crystal structure. Such optical resonances are known to occur at the wavelengths adjacent to the photonic band gap, sometimes referred to as the photonic band edge. The spatial arrangement and refractive indices of these structural domains generate photonic bands gaps that inhibit propagation of electromagnetic radiation centered about a particular frequency.

This anomalous resonant phenomenon (termed guided-mode resonance) arises due to the introduced periodicity which allows phase-matching of externally incident radiation into modes that can be reradiated into free-space. Due to the fact that these modes possess finite lifetimes within such structures, they are referred to as 'leaky eigenmodes' of the structures. More recently, guided-mode resonances have been studied in crossed gratings or two-dimensional (2D) photonic crystal (PC) slabs. The leaky nature of these modes has been exploited towards the development of light emitting diodes (LEDs) with improved extraction efficiency, biosensors (see Cunningham et al., *Colorimetric Resonant Reflection as a Direct Biochemical Assay Technique*, Sensors and Actuators B, 2002, 81, pgs 316-328 (2002)) and vertically emitting lasers.

The ability of photonic crystals to provide high quality factor (Q) resonant light coupling, high electromagnetic energy density, and tight optical confinement can also be exploited to produce highly sensitive biochemical sensors. Here, Q is a measure of the sharpness of the peak wavelength at the resonant frequency. Photonic crystal biosensors are designed to allow a liquid test sample to penetrate the periodic lattice, and to tune the resonant optical coupling condition through modification of the surface dielectric constant of the crystal through the attachment of biomolecules or cells. Due to the high Q of the resonance, and the strong interaction of coupled electromagnetic fields with surface-bound materials, several of the highest sensitivity biosensor devices reported are derived from photonic crystals. Such devices have demonstrated the capability for detecting molecules with molecular weights less than 200 Daltons (Da) with high signal to noise margins, and for detecting individual cells. Because resonantly coupled light within a photonic crystal can be effectively spatially confined, a photonic crystal surface is capable of supporting large numbers of simultaneous biochemical assays in an array format, where neighboring regions within ~10 µm of each other can be measured independently. See Li, P., B. Lin, J. Gerstenmaier, and B. T. Cunningham, *A new method for label-free imaging of biomolecular interactions*. Sensors and Actuators B, 2003.

Given substantial advances in their fabrication and their unique optical properties, photonic crystal-based sensors are under development for a variety of applications. Biosensors are one application. Biosensors incorporating photonic crystal structures are described in the following references, which are hereby incorporated by reference in their entireties: U.S. Pat. Nos. 7,118,710, 7,094,595, and 6,990,259; U.S. Published applications 2007/0009968; 2002/0127565; 2003/0059855; 2007/0009380; 2003/0027327; Cunningham, B. T. J. Qiu, P. Li, J. Pepper and B. Hugh, *A Plastic calorimetric Resonant Optical Biosensor for Multi-parallel Detection of Label Free Biochemical Interactions*, Sensors and Actuators B, 2002, 85, pgs 219-226.

U.S. Pat. No. 6,707,561 describes a grating-based biosensing technology that is sometimes referred to in the art as Evanescent Resonance (ER) technology. This technology employs a submicron scale grating structure to amplify a fluorescence signal, following a binding event on the grating surface, where one of the bound molecules carries a fluorescent label. ER technology enhances the sensitivity of fluorophore based assays enabling binding detection at analyte concentrations significantly lower than non-amplified assays.

ER technology uses grating generated optical resonance to concentrate laser light on the grating surface where binding has taken place. In practice, a laser scanner sweeps the sensor at some angle of incidence (θ), typically from above the grating, while a detector detects fluoresced light (generally at longer optical wavelength) from the sensor surface. By design, ER grating optical properties result in nearly 100% reflection, also known as resonance, at a specific angle of incidence and laser wavelength (λ). Confinement of the laser light by and within the grating structure amplifies emission from fluorophores bound within range of the evanescent field (typically 1-2 µm). Hence, at resonance, transmitted light intensity drops to near zero.

The spectral width and wavelength of the resonance phenomena describes the important externally measurable parameters of a device. Resonance width refers to the full width at half maximum, in wavelength measure, of a resonance feature plotted as reflectance (or transmittance) versus wavelength. Resonance width also refers to the width, in degrees, of a resonance feature plotted on a curve representing reflectance or transmittance as a function of θ. In practice, one can make adjustments to the incident angle to "tune" the resonance towards maximum laser fluorophore coupling.

In one embodiment of this invention, a biosensor is constructed as a photonic crystal structure which has a periodic surface grating in which a so-called evanescent resonance is created. Conceptually, resonance phenomena can occur in planar dielectric layer gratings where almost 100% switching of optical energy between reflected and transmitted waves occurs when the grooves of the grating have sufficient depth and the radiation incident on the corrugated structure is at a particular angle. This phenomenon is exploited in the sensing area of the platform where that sensing area includes grating structures (e.g., grooves, or holes or posts) of sufficient depth and light is caused to be incident on the sensing area of the platform at an angle such that evanescent resonance occurs in that sensing region. This creates in the sensing region an enhanced evanescent field which is used to excite samples under investigation. It should be noted that the 100% switching referred to above occurs with parallel beam and linearly polarized coherent light and the effect of an enhanced evanescent field can also be achieved with non-polarized light of a non-parallel focused laser beam. Excitation photons incident on the sample (chip, for example) under resonance conditions couple into a thin corrugated surface (such as a metal oxide layer) at the site of incidence. As a result of the transducer geometry, the energy is locally confined into the thin corrugated layer of high refractive index material. Consequently, strong electromagnetic fields are generated at the surface of the chip. The effect has been attributed as evanescent resonance and leads to increased fluorescence intensity of chromophores (fluorescent material) close to the surface of the sensor. The effective field strength can be increased up to 100-fold by the confinement of the available excitation energy, depending on the optical properties of the optical detection system used.

The inventive sensors and method of this disclosure are useful in conjunction with a variety of different types of fluorophores. Such fluorophores have excitation and emission spectra which are typically well characterized and available from the manufacturer, or can be determined experimentally.

Quantum Dots (QDs) are fluorescent, nanometer-sized inorganic semiconductor crystals that have rapidly emerged as an important class of nanomaterials which promise to revolutionize a wide range of nanotechnology-enabled fields. QDs derive their unique optical properties (broad absorption spectrum, narrow, size-tunable emission spectrum, high photostability, quantum efficiency and strong nonlinear response) from quantum confinement effects. These attributes, coupled with the ability to functionalize QDs, has made them important candidates for light sources, solar cells, optical switches and fluorescent probes in sensitive biological assays. The ability to more efficiently excite and extract the light emitted by QDs would thus be of vital importance in realizing high brightness light sources, enhanced nonlinear effects and lowering the detection limits in biological assays.

Fluorescent dyes represent a broad class of organic and inorganic fluorescent molecules that are capable of emitting light. Generally, electrons within the fluorescent molecule are excited from a ground state to an excited state through the absorption of a photon from an external source of illumination. The electron in the excited state may return to the ground state through a variety of mechanisms. One such mechanism is through the release of heat in the form of a phonon. Another such mechanism is through the release of light in the form of a photon. Absorption of energy by the fluorophore occurs at a particular range of incident photon energies (or equivalently wavelengths) that are unique for each type of molecule. Due to conservation of energy, the emitted photon energy must be less than or equal to the energy of the incident photon, and therefore the emitted wavelength must be larger than the incident photon wavelength. Therefore, a fluorescent molecule has two distinct spectra associated with it: the range of wavelengths for which it is capable of absorbing photons, and the range of wavelengths for which it is capable of emitting photons. The difference between the absorption and emission wavelength is known as the Stokes shift.

SUMMARY

Photonic crystal sensors are disclosed for use in testing samples in which a fluorophore, e.g., inorganic crystalline semiconductor ("quantum dot") or fluorescent dye is present in the sample. The sample and fluorescent dye are in close proximity, or more typically bound, to the photonic crystal surface, e.g., by depositing the sample with fluorophore on the sensor surface in a dry or aqueous environment.

In one aspect of this disclosure, the photonic crystal sensor is constructed and arranged with a surface in the form of a periodic surface grating structure which simultaneously exhibits multiple resonance modes for light at a given incident angle. The resonance modes overlap both the excitation and emission spectra of the fluorophore. In particular, when light is incident upon the photonic crystal at an appropriate incident angle θ, the photonic crystal sensor simultaneously exhibits multiple resonance modes (referred to herein as leaking eigenmodes or leaky modes) which have spectra that overlap both the absorption (excitation) and emission spectra of the fluorophore present in the sample. In this document, the term "spectrum" in the context of a resonant mode refers to the band of wavelengths of incident light in which a guided mode resonance is created in the photonic crystal as the angle of incidence θ varies. A photonic crystal constructed and arranged so as to possess such a doubly resonant scheme (i.e., exhibiting resonance modes overlapping both the excitation and emission spectra of the fluorophore simultaneously at a given incident angle θ) yields strongly enhanced fluorescent emission and the ability to extract such emission in a highly efficient manner, resulting in a high sensitive sensors suitable for a very broad range of applications, as will be explained below.

A sample testing system for testing a sample having a fluorophore bound to the sample is also described. The testing system includes a detection instrument comprising a light source and a detector; and a photonic crystal sensor having a periodic grating structure. The sample including the fluorophore is placed on the periodic grating structure. The light source of the detection system is oriented relative to the photonic crystal sensor such that the light source illuminates the photonic crystal sensor at a incident angle θ in which the photonic crystal simultaneously exhibits a plurality of resonant modes, the resonant modes including an excitation mode having a first resonant spectrum and an extraction mode having a second resonant spectrum. The periodic grating structure is constructed and arranged such that the resonant spectrum of the photonic crystal in the excitation mode at least partially overlaps the excitation spectrum of the fluorophore and the resonant spectrum in the extraction mode at least partially overlaps the emission spectrum of the fluorophore. The detector operates to detect radiation from the fluorophore in the emission spectrum.

A method of testing a sample with a fluorophore present in the sample with the photonic crystal sensors of this disclosure are also described. The method includes the step of placing the sample onto the surface of a photonic crystal sensor; illuminating the photonic crystal biosensor with light at an angle of incidence θ, the biosensor responsively and simultaneously exhibiting (1) an excitation resonance mode having a spectrum which at least partially overlaps the excitation spectrum of the fluorophore; and (2) an extraction resonance mode having a spectrum which at least partially overlaps the emission spectrum of the fluorophore, the illumination and the resulting excitation and extraction resonance modes causing the fluorophore to emit light; and collecting the emitted light from the fluorophore and directing the emitted light onto a detector.

In yet another aspect, a photonic crystal sensor is disclosed which includes a periodic surface grating structure which exhibits a resonance mode at a given incident angle which overlaps the emission spectrum of a fluorophore which is present with a sample deposited on the sensor, and does not have a resonance mode which overlaps the excitation spectrum of the fluorophore. The photonic crystal sensor produces an enhanced extraction effect without also producing an enhanced excitation effect. Sample testing systems suitable for the doubly resonant photonic crystal sensors are also useful with this embodiment.

BRIEF DESCRIPTION OF THE FIGURES

FIG. 2b shows Scanning Electron Micrograph (SEM) images of a cleaved photonic crystal device of FIG. 2a. In FIG. 2a, the lines joining the features Γ, X and M are axes of high symmetry in the photonic crystal surface. $\Lambda=300$ nm is the period of the surface grating structure (with a square unit cell in X and Y directions) and t=125 nm, the thickness of a high index of refraction material layer which is deposited onto the grating layer. $\Theta$ is the angle the incident beam of light makes with the vertical.

FIGS. 5a, 5b and 5c are graphs of the dispersion spectrum showing the resonance modes of the photonic crystal sensor showing the possibility of enhanced extraction for all polarizations and directions of incident white light. The graphs were experimentally determined from the photonic crystal of FIG. 2a. FIG. 5a is the graph for P-polarized and incident along the Γ-M direction, FIG. 5b is the graph for P-polarized and incident along the Γ-X direction, and FIG. 5c is the graph for S-polarized, incident along Γ-X direction.

FIGS. 6a and 6b are fluorescence (pseudocolor) scan images of the photonic crystal of FIG. 2a with quantum dots dispensed on the surface. FIG. 6a is a scan image taken when the photonic crystal is resonant with respect to the incident beam ($\theta=11.2°$), showing an enhancement factor of over 108 times. FIG. 6b is a scan image taken when the photonic crystal is not resonant with the incident beam ($\theta=0°$), showing an enhancement factor of over 13 times. The circular regions represent the area over which intensity information was averaged. In both the images, the circle to the left shows the control region where no photonic crystal is present.

DETAILED DESCRIPTION

Figure 2A:
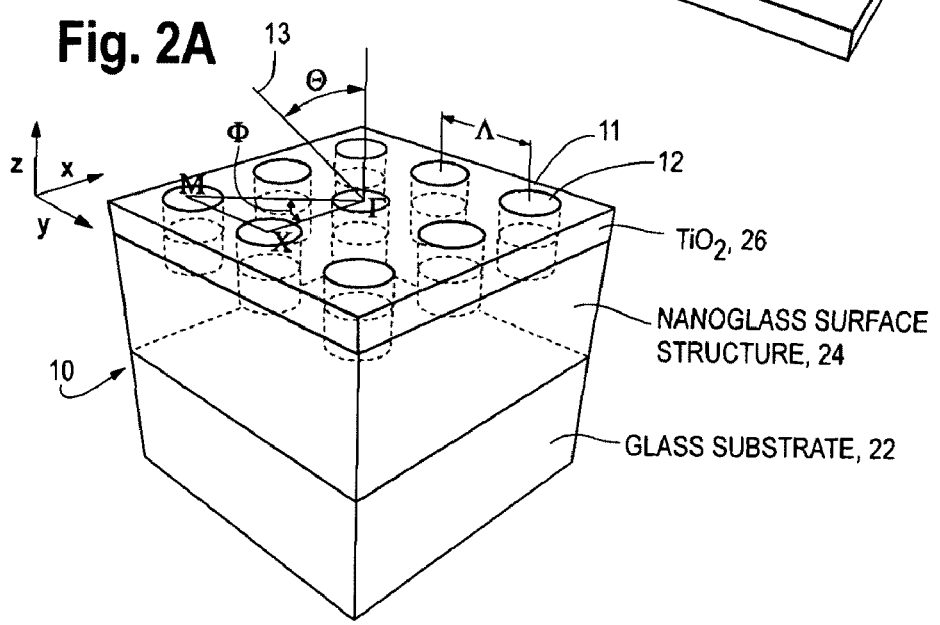
FIG. 2a is an illustration of a two-dimensional photonic crystal device having a periodic surface grating structure constructed as a two dimensional array of holes in accordance with one exemplary embodiment of the invention.

Photonic crystal sensors are disclosed for use in testing samples in which a fluorophore, e.g., inorganic crystalline semiconductor ("quantum dot") or fluorescent dye is present in the sample. The sample and fluorescent dye are in close proximity, or more typically bound, to the photonic crystal surface, e.g., by depositing the sample with fluorophore on the sensor surface in a dry or aqueous environment. An example of the photonic crystal is shown in FIG. 2a and will be described in detail subsequently.

In one aspect of this disclosure, the photonic crystal sensor is constructed and arranged with a surface in the form of a periodic surface grating structure (such as a two dimensional array of holes shown in FIG. 2a), which simultaneously exhibits multiple resonance modes for light at a given incident angle. The resonance modes are shown graphically in FIGS. 4 and 6 (transmission efficiency shown plotted as a function of wavelength for incident light at different angles to vertical), described subsequently, and are indicated in the areas of the graphs where the transmission efficiency drops to zero. The resonance modes overlap both the excitation and emission spectra of the fluorophore present in the sample. In particular, when light is incident upon the photonic crystal at an appropriate incident angle θ, the photonic crystal sensor simultaneously exhibits multiple resonance modes (referred to herein as leaking eigenmodes or leaky modes) which have spectra that overlap both the absorption (excitation) and emission spectra of the fluorophore present in the sample. A photonic crystal constructed and arranged so as to possess such a doubly resonant scheme (i.e., exhibiting resonance modes overlapping both the excitation and emission spectra of the fluorophore) to enhance fluorescent emission from the fluorophore has not, to the current knowledge of the inventors, been previously demonstrated.

The presence of the photonic crystal resonance peak occurring at the fluorescence excitation wavelength gives rise to the formation of high intensity electromagnetic near-fields which serves to efficiently excite the fluorophore present in the sample. This phenomenon is referred to herein interchangeably as "evanescent resonance" or "enhanced fluorescence."

The additional feature of a resonance mode in the photonic crystal which overlaps the emission spectrum of the fluorophore serves as an effective mechanism to extract this enhanced emission. In particular, a photonic crystal with resonance modes overlapping both the emission and excitation spectra of the fluorophore increases the number of fluorescence emitted photons which can be gathered by a detector in an associated measuring instrument for use with the photonic crystal sensor. Photonic crystal resonance occurring at the emission wavelength of the fluorophore can be used to efficiently couple emitted photons at the photonic crystal surface to be selectively directed into free space at a particular exit angle, instead of uniformly directed in all directions. This phenomenon of selective direction of emitted photons is believed to be due to fluorescence coupling to the overlapping leaky modes producing Bragg scattering out of the structure, thereby greatly reducing the amount of light trapped in the photonic crystal sensor in the extraction mode. If the dispersion of these overlapping emission leaky modes is close to the Γ-point band edge (i.e., the magnitude of the in-plane wave vector for incident polarized light is close to zero), a significant amount of the emitted light can be extracted from the photonic crystal sensor within small angles of the vertical. This discovery allows for positioning of a detector (or associated optical elements such as fiber optic probe which is coupled to a detector) at the correct position relative to the photonic crystal surface, and allows for capturing more photons that would otherwise occur, e.g., as compared to a fluorophore emitting from a non-photonic crystal surface.

Figure 1:
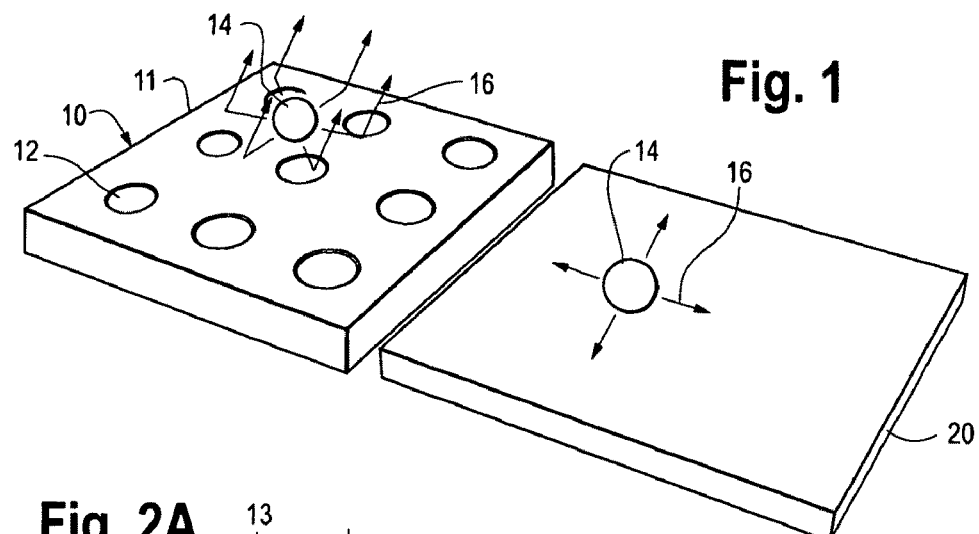
FIG. 1 is an illustration of a photonic crystal featuring the enhanced excitation and extraction features of this disclosure and comparing the directionally enhanced extraction of emitted radiation from fluorophores from the photonic crystal with a dielectric slab which does not feature the resonance modes of this disclosure.

A photonic crystal sensor as just described is shown in FIG. 1 as item 10, with a dielectric slab 20 shown next to it which does not possess a photonic crystal property for purposes of comparison. The photonic crystal sensor 10 consists of a periodic surface grating structure formed on its surface 11, which in this example takes the form of a two-dimensional array of holes 12. (Other periodic structures for the photonic crystal 10 are possible, as will be explained below). A sample containing a fluorophore 14 is applied to the surface 11. The photonic crystal is illuminated with light (in this case from above) at an angle θ relative to the vertical direction. The angle θ is shown in FIG. 2a. The properties of the periodic grating (holes) 14 on the surface 11 are such that the photonic crystal simultaneously exhibits resonance modes which overlap both the excitation and emission spectra of the fluorophore 14. The overlap of the resonance mode with the excitation spectrum produces an enhanced excitation of the fluorophore 14. The overlap of the resonance mode with the emission spectrum of the fluorophore 14 produces a directionally enhanced extraction of the emitted radiation due to Bragg scattering, which is indicated by the lines 16 all pointing in the same direction. As a practical matter, the angle of the lines 16 can be determined either by simulation or by experimentation and light collection apparatus placed in alignment with the lines 16 so as to collect this radiation. The light collection apparatus (e.g., fiber optic probe) supplies the collected radiation to a detection device such as a CCD imager or photomultiplier tube so as to make measurements or collect images of the radiation, thereby obtaining information as to the sample.

Consider now the dielectric slab 20 in FIG. 1 which does not possess any photonic crystal attributes for the sake of comparison. Assuming the incident light encompasses the excitation spectrum of the fluorophore 14, at least some fluorescence can be expected. However, because there is no resonant mode in the slab 20 overlapping the emission spectrum of the fluorophore, the resulting fluorescence is radiated in an almost spatially uniform manner, indicated by the lines 16 pointing in all directions. Thus, the concentration of radiation in the same direction as indicated at 16 on the left hand side of FIG. 1 produces an enhanced extraction of the fluorescent signal which is not present in a non-photonic crystal structure such as shown on the right hand side of FIG. 1. (While light can be directed onto the surface 11 from above, as shown in FIG. 1, it can also be incident on the photonic crystal from below and the same resonant effects are produced in the photonic crystal).

The gain in sensitivity in the photonic crystal sensor 10 of FIG. 1 obtained by (1) evanescent resonance (enhanced fluorescence due to one resonance mode of the photonic crystal overlapping the excitation or absorption spectrum of the fluorophore) and (2) enhanced extraction (due to another resonance mode of the photonic crystal overlapping the emission spectrum of the fluorophore) are multiplied together to derive the overall gain in sensitivity resulting from the combination of these features. For example, if the evanescent resonance provides for a hundred-fold increase in the amount of fluorescence emission, and the enhanced extraction provides the ability of the detector to collect a five times as many fluorescent photons, then the overall sensitivity of an assay performed on a photonic crystal surface using the combined techniques will be five hundred (500) times greater than the same assay performed on an ordinary surface (e.g., microscope slide, microplate or microfluidic flow channel) which does not possess the photonic crystal properties of this invention.

Thus, one benefit of a photonic crystal sensor 10 with the doubly resonant properties as described above is that it provides a sensor platform in which a very substantial increase in the sensitivity of fluorescent assays occurs than would otherwise be possible. As will be appreciated from the following detailed description, photonic crystal sensors in accordance with the invention are useful in a number of different applications. These include:

1) Gene expression microarrays incorporating the photonic crystal sensor 10. The genes may be detected at lower expression levels and or with smaller sample volumes than previously known.

2) Protein detection assays, such as for example detection of protein biomarkers in bodily fluids for disease diagnostic tests, where proteins are present in very low concentrations. Detection by the methods of this disclosure would be more sensitive than commonly use ELISA assays, but with a simpler assay protocol.

3) Fluorescent imaging of cells, viruses, tissue samples, bacteria, proteins etc., using a microscope. The photonic crystal sensor 10 of this disclosure can be incorporated onto the surface of a microscope slide. A specimen is stained with one or more fluorescent dyes or quantum dot fluorophores (which may be conjugated to an antibody or other probe of interest) and placed on the slide such that the specimen and fluorophore(s) are in contact with the surface of the photonic crystal sensor 10. The improved sensitivity can be used to observe dye molecules at lower concentrations and/or to use lower cost imaging cameras with an improved signal to nose ratio.

4) The photonic crystal sensor 10 can be produced uniformly over large surface areas using a nano-replica molding process which is suitable for mass production at low cost. The photonic crystal structure thus produced can be incorporated into the surface of various assay or testing devices of conventional formats, such as, for example, (1) incorporation onto the surface of a microscope slide, (2) incorporation within a standard format microplate, e.g., at the bottom thereof, or (3) incorporation into any other fluorescent assay format either now known or later developed.

Thus, in one embodiment of the invention, a sensor 10 is descried herein which is adapted to test a sample having a fluorophore present in the sample which is deposited on the sensor surface. The fluorophore (e.g. quantum dot, fluorescent dye such as Cy5) has an excitation spectrum and an emission spectrum. The sample may be placed on the sensor 10 in a dry or an aqueous environment. The sensor includes a photonic crystal having a periodic grating structure (12). The photonic crystal exhibits a plurality of resonant modes when illuminated with light at an incident angle θ. The resonant modes include an excitation mode having a first resonant spectrum and an extraction mode having a second resonant spectrum. The periodic grating structure is constructed and arranged such that the first resonant spectrum of the photonic crystal in the excitation mode at least partially overlaps the excitation spectrum of the fluorophore and the second resonant spectrum of the photonic crystal in the extraction mode at least partially overlaps the emission spectrum of the fluorophore.

In one embodiment, the extraction resonant mode of the photonic crystal at the incident angle exhibits a relatively low Q factor, i.e., one in which the Q factor is less than 100. The Q factor of the extraction mode will determine the rate at which coupled radiation will be scattered into free space, such as in the case where the fluorophore exhibits a broad emission spectrum. In other embodiments, the extraction resonant mode has a Q factor is relatively high, i.e., between 100 and 1000. With a relatively high Q factor, a detector can obtain enhanced extraction from a narrow band of wavelengths, but with amplified extraction efficiency. A sensor constructed to produce the optimum Q factor at the extraction resonant mode for a given application will depend on several factors, such as 1) whether the sensor is designed to be used in a detection instrument which performs single-point detection (with a photomultiplier tube, as an example) where one can gather a broad range of wavelengths with a broad range of exit angles, situations where a low Q factor for the extraction resonant mode might be best, and 2) whether the sensor is designed to be used in a detection instrument which performs imaging detection (e.g., with a CCD camera), in which case a relative high Q factor would provide detection of a narrow range of wavelengths and a narrow range of exit angles for that wavelength. The Q factor for the extraction resonance mode can be changed by changing the parameters of the surface grating structure and simulated in the design phase as will be described below.

The sensor as described herein can be incorporated into testing platforms suited to a variety of specific applications. In one example, the sensor is incorporated into a gene expression microarray device. In another example, the sensor is incorporated into a protein detection assay device and the sample is in the form of a protein. In still other examples, the sensor is incorporated into a testing device, such as a microscope slide, which is used to perform fluorescent image analysis of cells, viruses, bacteria, spores, and tissue samples. In still another example the sensor is incorporated into a microwell plate having a plurality of individual sample wells. Each of the sample wells includes a photonic crystal as described herein.

In one particular embodiment, the periodic surface grating structure of the photonic crystal is constructed as a grating layer arranged as a two-dimensional array of holes each having a depth D, and a relatively high index of refraction material of thickness t deposited on the grating layer. Suitable high index of refraction materials include titanium oxide ($TiO_2$), silicon nitride, hafnium oxide, zinc sulfide, tantalum oxide and zinc selenide. In preferred embodiments the array of holes has an axis of symmetry which is either perpendicular or parallel to the polarization state of the incident light. In FIG. 2a, the lines connecting the features Γ, X and M are axis of high symmetry in the photonic crystal surface. The grating layer is positioned above a substrate layer. The substrate layer may consist of a layer of glass, quartz, polymers, plastic, polyethylene terepthalate (PET) and combinations thereof.

The depth D of the holes can be selected such that the photonic crystal exhibits the excitation and extraction resonance modes having spectra which are spectrally separated from each other and which substantially overlap the excitation and emission spectra, respectively, of a predetermined fluorophore, such as a particular quantum dot or group of quantum dots or other fluorophores having similar excitation and emission spectra.

In another aspect of this invention, a sample testing system is described for testing a sample having a fluorophore present in the sample which is deposited on the photonic crystal sensor. The fluorophore has an excitation spectrum and emits fluorescence in an emission spectrum. The sample testing system includes a detection instrument comprising a light source and a detector, and a photonic crystal sensor comprising a periodic grating structure. The sample including the fluorophore are placed on the periodic grating structure.

The particular construction of the detection system is not particularly important and can vary widely, depending on the particular application. Examples of suitable detection systems include those systems described in U.S. Pat. Nos. 7,118, 710, 7,094,595, and 6,990,259 and U.S. Published applications 2007/0009968; 2002/0127565; 2003/0059855; 2007/0009380; and 2003/0027327.

The light source of the detection system is oriented relative to the photonic crystal sensor such that the light source illuminates the photonic crystal sensor at a incident angle θ in which the photonic crystal simultaneously exhibits a plurality of resonant modes, the resonant modes including an excitation mode having a first resonant spectrum and an extraction mode having a second resonant spectrum.

The periodic grating structure is constructed and arranged such that the first resonant spectrum of the photonic crystal in the excitation mode at least partially overlaps the excitation spectrum of the fluorophore and wherein the second resonant spectrum of the photonic crystal in the extraction mode at least partially overlaps the emission spectrum of the fluorophore.

In one embodiment, the detector may take the form of an imaging detector, e.g., charge coupled device (CCD) camera. Other types of detectors are also possible, including photomultipliers. In preferred embodiments the light source may be a laser or a broad spectrum source. The light from the source may be polarized. In one embodiment, the grating structure of the photonic crystal has an axis of symmetry which is substantially parallel or perpendicular to the polarization state of the incident light.

The sensor can be incorporated into a variety of different testing device formats, as explained herein, such as a gene expression microarray device, a protein detection assay device, a microscope slide, and a microwell plate or dish having a plurality of individual sample wells, in which each of the sample wells includes a photonic crystal described herein.

In a further aspect, a method is disclosed of testing a sample having a fluorophore bound to the sample, the fluorophore having an excitation spectrum and an emission spectrum, comprising the steps of: (a) placing the sample onto the surface of a photonic crystal sensor, (b) illuminating the photonic crystal biosensor with light at an angle of incidence θ, the biosensor responsively and simultaneously exhibiting (1) an excitation resonance mode having a spectrum which at least partially overlaps the excitation spectrum of the fluorophore; and (2) an extraction resonance mode having a spectrum which at least partially overlaps the emission wavelength distribution of the fluorophore, the illumination and the resulting excitation and extraction resonance modes causing the fluorophore to emit light, and (c) collecting the emitted light from the fluorophore and directing the emitted light onto a detector.

Example

FIG. 2a is an illustration of a photonic crystal sensor 10 in accordance with one embodiment of the invention. The sensor 10 includes a glass substrate layer 22, a grating layer 24 providing a periodic grating structure (in this case a two dimensional array of holes 12) and a high index of refraction layer 26 of $TiO_2$ which is deposited on the grating layer 24.

In order to design a PC that can support multiple guided-mode resonances, a two-dimensional structure with a sufficiently large effective index and the features arranged as a square lattice of holes was chosen, as shown in FIG. 2a. The period (Λ) of the structure was chosen such that it supports a relatively high Q-factor resonant modes at a wavelength where the fluorophores (in this instance, quantum dots) are excited (λ=488 nm, excitation mode) and low Q-factor modes overlapping the quantum dot fluorescence emission spectrum (centered at λ=616 nm, extraction mode). In FIG. 2a, the features Γ, X and M are points of high symmetry in the photonic crystal surface. Λ=300 nm is the period of the surface grating structure (with a square unit cell in X and Y directions) and t=125 nm, the thickness of a high index of refraction material layer 26 which is deposited onto the grating layer 24. Θ is the angle the incident beam of light 13 makes with the vertical (direction normal to the surface 11).

Figure 2B:
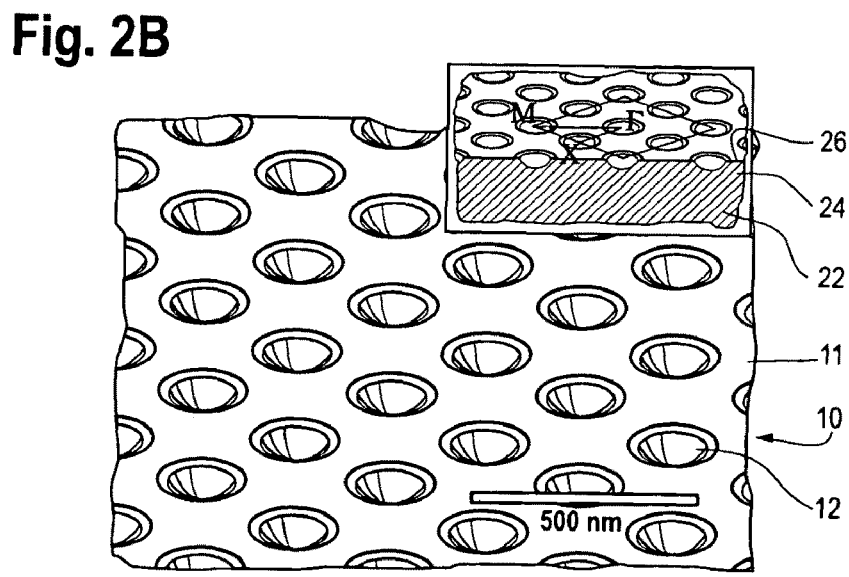

The logic governing the choice of low Q-factor extraction modes for some embodiments will become clear shortly, and although a relatively low Q-factor resonance mode at the emission spectrum is shown (Q<100) in other applications a relatively high Q-factor (100≦Q<1000) may be desired. The depth "D" of the holes 12 was chosen to provide the required spectral separation between the excitation and extraction modes. The thickness 't' of the $TiO_2$ high index layer 26 was chosen to fine tune the spectral location of the resonant modes. The photonic crystal sensor of FIG. 1a was cost-effectively fabricated by a nano-replica molding approach in an asymmetric configuration, so as to provide the required mechanical stability and maintain a simplistic fabrication procedure. A combination of high refractive index (RI) material (layer 26) and low refractive index material (layer 24, "Nanoglass"™, Honeywell) was important in order to provide sufficient effective index and positioning of the modes, respectively. Using a low RI material for layer 24 allows the modes to be positioned closer to the device's upper surface 11, whereas a high RI material for layer 24 which would draw the modes deeper into the device 10 and subsequently reduce their interaction with the fluorophores. The top surface 11 and cross section SEM images of a fabricated model device are shown in FIG. 2b. The selection of parameters of the device (refractive index, thickness, periodicity, etc.) can be chosen to provide the desired location of resonant modes, as further described herein.

While an array of holes is shown in the embodiment of FIG. 2a, other types of periodic structures are possible. Such structures generally have a configuration of periodic high and low regions (referred to herein occasionally as "grooves"), which can take a variety of forms. In one embodiment, the thickness of the high index layer 26 is in the range 30 to 1000 nm, e.g. 50 to 300 nm, preferably 50-200 nm. The period of the corrugated structure may be in the range 200 to 1000 nm, e.g. 200 to 500 nm, preferably 250-500 nm. The ratio of the groove depth to the thickness of the high index layer 26 lies in the range 0.02 to 1 e.g. 0.25 to 1, preferably 0.3 to 0.7, and the ratio of the grooves width to the period of the grooves ("duty-cycle") lies in the range 0.2 to 0.8, e.g. 0.4 to 0.6. Increasing the thickness of the high refractive index layer 26, the refractive index of the layer 26, the refractive index of the low index periodic grating layer 24, or the period of the grating will tend to increase the wavelength of the resonant mode.

The grooves may be generally rectangular in cross-section. Alternatively, the grooves may be sinusoidal or of saw tooth cross-section. The surface structure may be generally symmetrical. Preferred geometries include rectangular, sinusoidal and trapezoidal cross-sections. Alternatively, the grooves may be of saw tooth cross-section (blazed grating) or of other asymmetrical geometry. In another aspect the groove depth may vary, e.g. in periodic modulations.

The support or platform may be square or rectangular and the grooves may extend linearly along the platform so as to cover the surface. Alternatively the platform may be disc shaped and the grooves may be circular or linear.

The grating structure can take variety of one and two dimensional forms, including two-level, two dimensional gratings, as disclosed in published PCT application WO 2007/0179024, the contents of which are incorporated by reference herein. These include square lattices and hexagonal lattices that have symmetry in three directions along the planar surface of the structure.

The corrugated, periodic grating surface may be optimized for one particular excitation wavelength and for one particular type of polarization. By appropriate means, e.g. superposition of several periodic structures which are parallel or perpendicular one with another, periodic surface relief can be obtained that are suitable for multiple wavelength use of the photonic crystal sensor ("multicolor" applications). Alternatively, individual sensing areas on one platform may be optimized for different wavelengths and/or polarization orientations.

In another embodiment, the photonic crystal is constructed so as to exhibit a first extraction resonance mode in a first spatial area of the photonic crystal and a second extraction resonance mode in a second spatial area of the photonic crystal distinct from the first spatial area. In other words, the construction of the surface grating structure can vary spatially (in X and Y directions) such that different areas of the photonic crystal exhibit different extraction resonant modes. This spatial pattern of different extraction modes can be repeating. The first extraction resonance mode has a spectrum at least partially overlapping the emission spectrum of a first predetermined fluorophore (e.g., a particular quantum dot) and wherein the second extraction resonance mode has a spectrum at least partially overlapping the emission spectrum of a second predetermined fluorophore different from the first predetermined fluorophore (e.g., a second quantum dot).

Additionally, the construction of the surface grating structure 12 can vary spatially (in X and Y directions) such that different areas of the photonic crystal exhibit different extraction resonant modes. As an example, the photonic crystal exhibits different excitation resonant modes at different spatial regions on the surface so that the fluorescent dye Cy5 is excited in one location; and the fluorescent dye Cy3 is excited in another nearby location. One could alternate between a group of fluorophores (red, green, blue) much like how a single pixel of a video display is comprised of multiple color emitters arranged close to each other.

In another possible embodiment the photonic crystal is constructed so as to exhibit a plurality of extraction resonance modes, each of the plurality of extraction resonance modes having a resonant spectrum at least partially overlapping an emission spectrum of a different predetermined fluorophore.

Enhanced Excitation

Figure 4A:
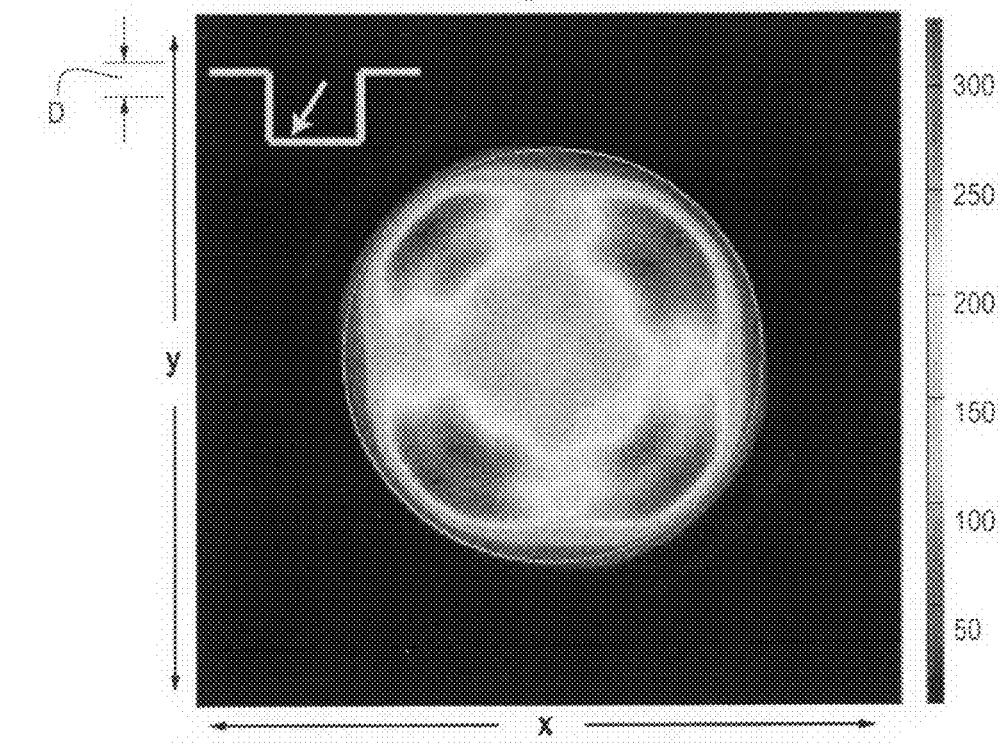
FIGS. 4a and 4b are calculated near electric-field intensities ($E^2$) at resonance for the photonic crystal structure of FIG. 2a, with FIG. 4a showing the intensity for the lower surface of the surface grating (bottom of the hole) and FIG. 4b showing the intensity for the upper surface of the surface grating. The intensities are for the leaky mode (resonance) with $\lambda=488$ nm when the incident beam makes an angle $\theta=11.2°$ with the surface normal. The intensity is normalized to the unit amplitude incident wave.

When externally incident light 13 (FIG. 2a) interacts with periodically modulated structures (holes 12) in the sub-wavelength regime for a photonic crystal, only the $0^{th}$ order forward and backward diffracted waves can propagate. The periodicity however, also allows for phase-matching of higher (evanescent) orders to localized leaky modes supported by the photonic crystal 10. Once excited, the leaky modes, defined by a complex propagation constant, possesses a finite lifetime as they are leaked out both in the forward (transmitted) and backward (specular) directions. The backward reradiated waves are in phase and constructively interfere with the $0^{th}$ backward diffracted order while the forward reradiated waves are out of phase with the $0^{th}$ forward diffracted order by $\pi$ radians, causing destructive interference and consequently resulting in zero transmission. Thus, the external excitation of the leaky modes by means of incident light 13 (FIG. 2a) is associated with a 100% reflection phenomenon for the resonant wavelength, assuming a defect-free, lossless system. Since the excited leaky modes are radiative but localized in space during their finite lifetimes, they can be engineered to have very high energy density within regions of the photonic crystal at resonance. The magnitude of this energy density is directly related to the resonant mode lifetime or Q-factor of resonance, which in turn can be controlled by adjusting the device parameters (thickness, refractive index, depth of holes, periodicity, etc.). Therefore, the intensity of emission of a fluorophore (14, FIG. 1) (which is absorptive at the resonant wavelengths) can be greatly enhanced by placing the fluorophores in proximity to regions where the resonant modes concentrate most of their energy. In the example of FIG. 2A, this region is the bottom of the holes, as shown in FIG. 4a, as will be explained below.

Enhanced Extraction

Concurrently with the enhanced excitation as just described, the existence of leaky modes in the photonic crystal 10 that overlap the fluorescence emission spectrum opens up additional pathways for the emitted light to escape into free-space. Besides direct emission, the fluorescence can couple to the overlapping leaky modes and Bragg scatter out of the photonic crystal sensor, thereby greatly reducing the amount of light trapped as guided-modes, in comparison to an un-patterned substrate (as explained above in FIG. 1). If the dispersion of these overlapping emission leaky modes is close to the Γ-point band-edge, i.e. $K_{11}$ (magnitude of in-plane wave vector)~0, a significant amount of the emitted light will be extracted within small angles with the vertical. It can thus be appreciated that enhancement of fluorescence can be achieved by enhanced excitation and enhanced extraction acting in concert together at the same time.

Results for Example 1

Studying the reflection/transmission properties of a photonic crystal is a convenient technique to map out the dispersions of the leaky modes. Rigorous Coupled-Wave Analysis (RCWA) techniques were used to simulate how the device of FIG. 2a would respond in transmission to externally incident radiation.

Figure 3A:
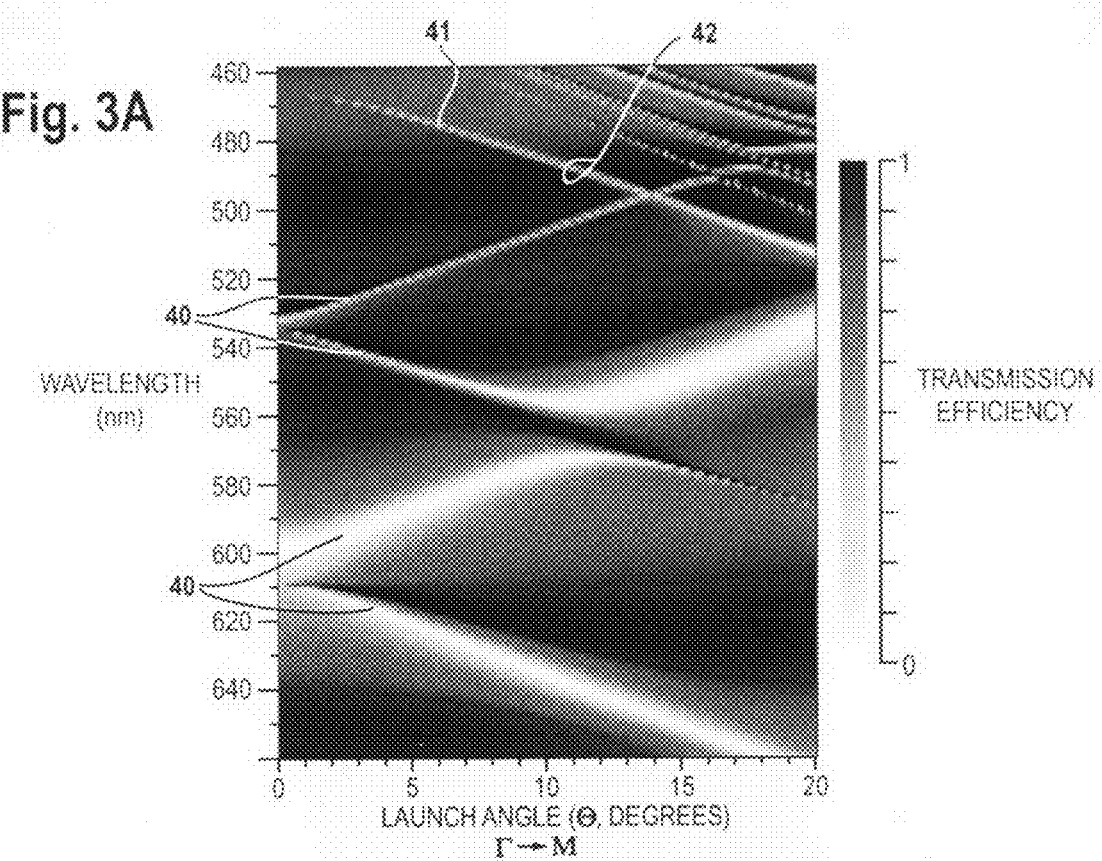
FIGS. 3a and 3b are graphs of the calculated and experimental dispersion spectra, respectively, of the fabricated photonic-crystal sensor of FIGS. 2a and 2b for white, S-polarized incident illumination incident along the Γ-M direction. The sensor exhibits resonant mode at $\lambda=488$ nm when the incident beam makes an angle $\theta=11.2°$ with the surface normal. The excitation of the resonant mode at this wavelength, where the quantum dot fluorophore is strongly absorbing, provides the required near-field enhancement for evanescent resonance (enhanced excitation). The shading scale shows the efficiency of transmission. Higher Q factors for a resonance mode are indicated by thinner lines whereas broader Q factors for a resonance mode are indicated by relatively thicker lines.
Figure 3B:
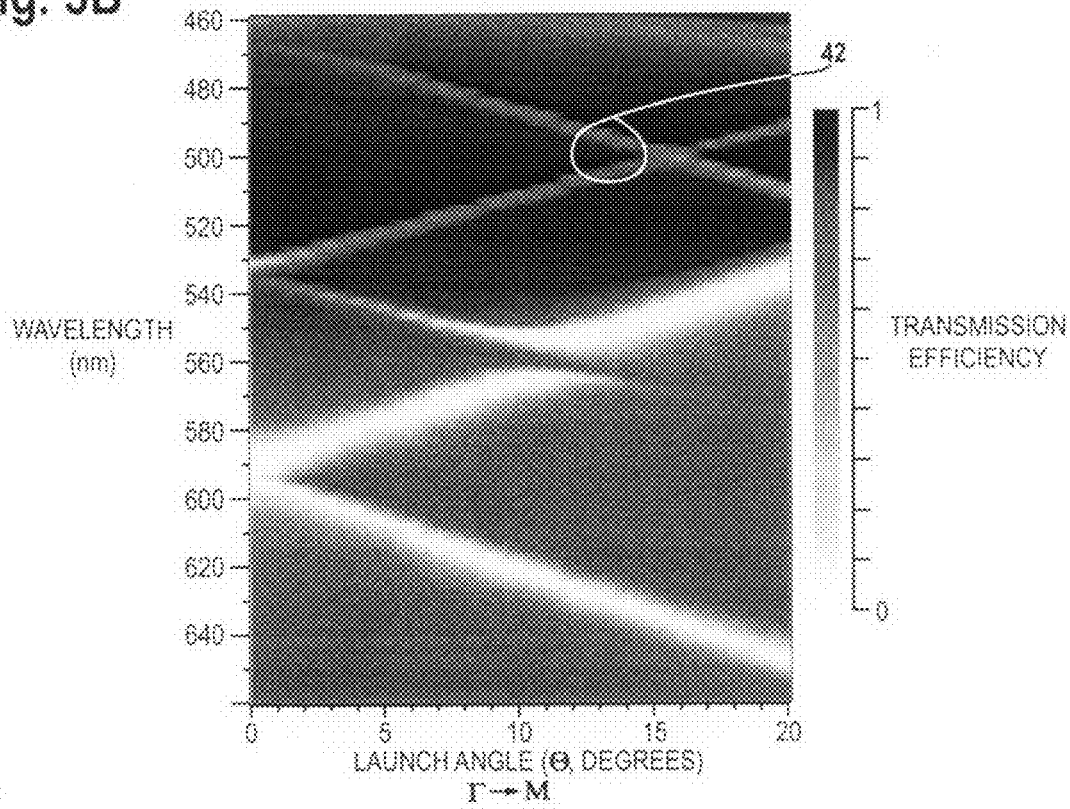

FIG. 3a shows the computed leaky mode band structure, i.e. spectral location and transmission efficiency of the resonances as a function of the angle of incidence (θ) of light 13 (FIG. 2a), along the Γ-M direction. As θ is increased from 0°, $K_{\parallel}$ begins to increase and results in degenerate resonances to separate into their respective constituent orders, as indicated at 40 in FIG. 3a. Experimental verification of the band structure of the fabricated device was carried out by mounting the device in a linear transmission setup, illuminating it with collimated white light and plotting the resulting transmitted spectrum as a function of θ, results of which are shown in FIG. 3(b). Excellent qualitative agreement between simulation and experiment in the 460 nm 500 nm range was seen, where the RIs of the materials vary slowly. Theoretically, it was predicted that the resonance at λ=488 nm should occur at θ=11.2° (the resonance indicated the region 42 in FIG. 3a), and this is accurately observed in experiment. At shorter wavelengths, the RI of $TiO_2$ begins to increase divergently ($n_{TiO2}$=2.7 at λ=400 nm) and is considerably less at longer wavelengths ($n_{TiO2}$=2.36 at λ=600 nm), leading to deviations from simulations assuming a constant RI ($n_{TiO2}$=2.46 at λ=488 nm). This is clearly seen in the theoretically predicted higher order bands originating from shorter wavelength resonances and red-shifted longer wavelength bands, which experimental results do not agree with. For the excitation mode shown in FIG. 3A, the Q-factor of resonance was found to be ~155. The relatively high Q-factor is indicated in FIG. 3a by the thin, highly defined line 41 of zero transmission efficiency in the region 42.

Figure 4B:
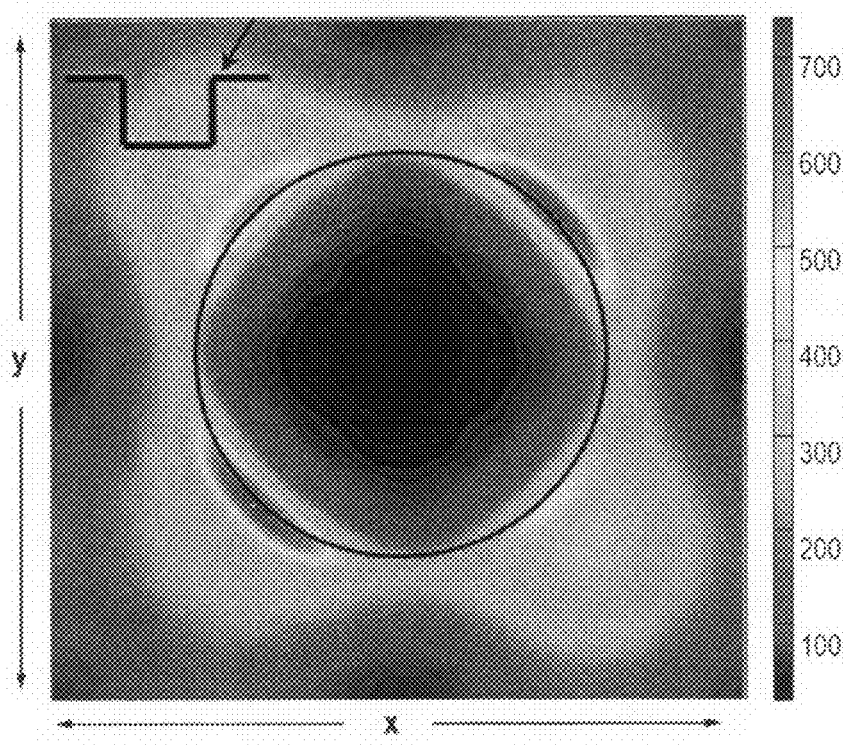

FIGS. 4a and 4b show the simulated electric near-field intensity ($E^2$) (normalized to the unit amplitude incident field) at the two available surfaces of the device, for the excitation of the resonant mode at λ=488 nm. FIG. 4a shows the intensity at the bottom of the holes 12 of FIG. 2a. FIG. 4b shows the intensity at the upper surface 11 of the sensor 10. The influence of the resonance phenomenon on the resulting near-fields is clearly seen as manifested in the enhanced electric field intensity. Similar enhancement can also be seen for the magnetic near-fields. It is apparent that for the lower available surface (FIG. 4a) (bottom of the hole) the excitation mode concentrates its energy within the cavity region (the term cavity is used here strictly in relation to the shape of the cross-section). At the upper surface (FIG. 4b), the energy is concentrated at the cavity periphery and beyond. Both the bottom of the well and the areas on the surface 11 adjacent to the holes are where the fluorophore will be present during use, hence the device exhibits strong intensities in the excitation resonance mode in the areas of interest. Above the surfaces shown in FIGS. 4a and 4b, the field intensity decays exponentially (as previously shown). In practice, with a finite fluorophore which is not at the surface and unavoidable losses, the exact near-field intensity available to the fluorophore will always be lower than shown in FIGS. 4a and 4b.

The amount of amplification for enhanced excitation detection is related to the power transferred from the device structure to a distribution of fluorophores on the sensor surface at the excitation wavelength of the fluorophore. The power density distribution of the sensor surface at the resonant wavelength, provided that the resonant wavelength is matched to the excitation wavelength, therefore provides a means for comparing the sensitivity of different device designs. One can define the cross product E (max)×H (max) as a field power or "magnification factor". While a more thorough analysis of the intensity distribution of the evanescent field from the tops, bottoms, and sides of the structure, and a detailed integration of power density to account for differences between higher and lower power regions would provide a more exact prediction of whether one device will function more effectively than another, the product of the maximum magnitude of an E component with an orthogonal H component provides a very simple, rough way of comparing designs. Nevertheless, studying the near-field intensity at the available surfaces gives a convenient metric to optimize the photonic crystal design. In this case, it is also important to mention that due to the inherent asymmetry of the photonic crystal, the mode concentrates its energy in the high index layer (26) and is biased more towards the grating layer below it. By reversing the asymmetry (that is, by flooding the device surface with higher index material, such as water) we can reverse this biasing and to an extent, 'draw' the resonance mode closer to the device surface, therefore further increasing the mode interaction with the fluorophore. Such a modification will be easily adaptable for enhanced fluorescence biosensors, for example, where the analytes bound to the fluorophores are typically in an aqueous buffer solution. Near-field scanning optical microscopy (NSOM) images of the fabricated devices excited close to the resonant wavelength have confirmed enhancement and spatial localization of the electric field intensity.

Figure 5A:
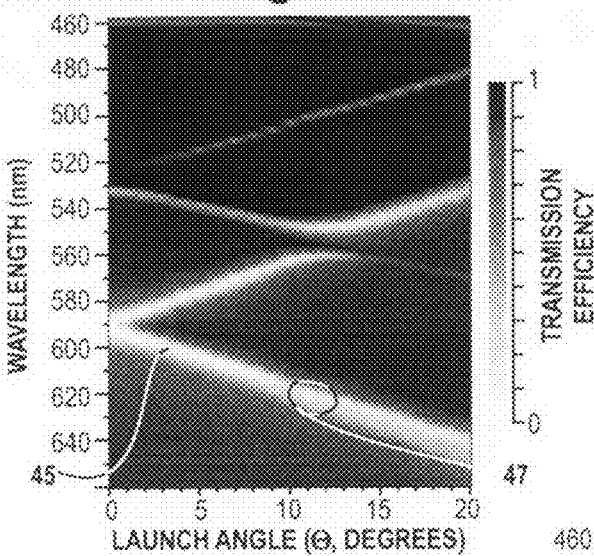
Figure 5B:
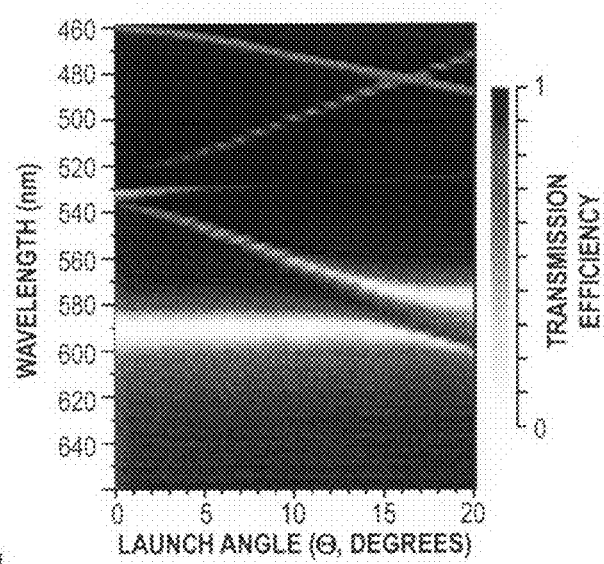
Figure 5C:
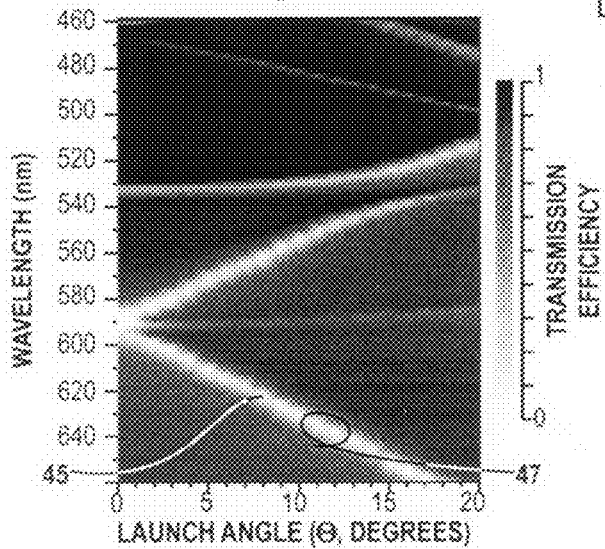

The effect of the leaky modes that overlap the emission spectrum of the fluorophores, which as per design, provide maximum overlap close to the Γ-point band-edge, will now be discussed. Such a choice is easily justified for maximal near-vertical extraction. In this enhanced extraction phenomenon, the Q-factor of the extraction modes will determine the rate at which coupled radiation will be scattered into free-space. A low Q-facfor (implying a short mode lifetime) would be beneficial in some applications, as the coupled radiation can be scattered faster and thus the interaction of the radiation with losses in the system can be limited. A low Q-factor is also desirable from the standpoint that the radiation emitted from the fluorophores has a finite bandwidth, and a broad leaky resonance can scatter more of the emitted wavelengths in a given direction. Since the polarization and directions of the emitted fluorescence for a fluorophore (e.g., quantum dot) in free-space can be assumed to be arbitrary, the various available leaky modes that can interact with the emitted light are considered. The experimentally determined dispersion of the leaky modes supported by the photonic crystal in the Γ-X and Γ-M directions and for orthogonal polarizations (S and P) is shown in FIGS. 5a, 5b and 5c. (If an electromagnetic wave is propagating toward a sensor surface at an angle, it will have two orthogonal components of electric field. The "S" component is the one with the electric field vector oriented parallel to the sensor surface (so one can think of "S" standing for "skim", since the electric field vector skims the surface), whereas the "P" component is the electric field component with the vector oriented directly into the sensor surface, and one can think of P as standing for "Plunge" as the electric field vector plunges into the sensor surface. Incident light can have both components at the same time.)

The case involving Γ-M and S polarization is already shown in FIG. 3(a). It is clearly seen that the QD fluorophore whose emission spectrum is (centered at λ=616 nm) can couple to leaky modes supported by the photonic crystal and be extracted out of the device, because the photonic crystal has a resonance mode indicated by the line 45 in FIGS. 5a and 5c which includes a region of resonance indicated at 47 which includes λ=616 nm at the angle of incidence 11.5 degree. From experiment, the Q-factor for the extraction modes was ~92.

To quantify the effects of the two fluorescence enhancement schemes, the fabricated devices were cleaned using de-ionized water/isopropyl alcohol, and the QDs (CdSe/ZnS core-shell type, Evident Technologies, peak emission at λ=616 nm) were diluted in toluene and made up to a concentration of 1.235 nM. The dilute solution of QDs was dropcast on and off (to serve as a reference) the photonic crystal surface. After the drying of the spots, the devices were scanned on a commercially available laser scanner (LS 2000, Tecan), equipped with a 25 mW, 488 nm solid-state laser and a photo multiplier tube (PMT) to record the fluorescence signals. The scanner provides the ability to launch the incident illumination at angles tunable from 0° to 25° in steps of 0.1°, along a single vertical axis and single polarization. In order, to quantify the extraction enhancement and the excitation enhancement effects, the devices were scanned at the resonant angle (θ=11.2°) and a non-resonant angle (θ=0°). For the sake of clarity, the resonant angle is defined as the launch angle (θ) for which the leaky mode at λ=488 nm is excited. FIGS. 6a and 6b show the scanned images taken at θ=11.2° and θ=0° respectively. The circular regions 50 on the images show the areas over which intensity information was averaged. Table 1 shows the raw data measured in PMT counts for the two cases over multiple measurements. "PC" in Table 1 indicates "photonic crystal."

TABLE 1

| | Signal | | Background | |
|---|---|---|---|---|
| | On PC (S1) | off PC (S2) | on PC (B1) | off PC (B2) |
| θ = 11.2° | 10,160.93 ± 362.92 | 131.78 ± 2.91 | 336.03 ± 9.14 | 41.52 ± 1.13 |
| θ = 0° | 705.31 ± 8.80 | 72.53 ± 0.93 | 25.33 ± 0.89 | 21.04 ± 0.48 |

The enhancement (calculated by (S1−B1)/(S2−B2)) for θ=11.2° was 108.89±4.09, and for θ=0° was 13.21±0.26. The observed enhancement at θ=0° is attributed mainly to the enhanced extraction provided by the photonic crystal. Since the extraction effect is only related to the dispersive properties of the photonic crystal, it should not be affected by a change in the launch angle of the incident light. Using this assumption, the total enhancement obtained for the resonant angle is divided by the enhancement obtained for the non-resonant angle and a value of 8.24±0.36 times for fluorescence enhancement by the near-fields was obtained.

DISCUSSION

The result for fluorescence enhancement due to the enhanced near-fields, at first glance, is much lesser than the peak intensity of the near-fields shown in FIGS. 4a and 4b. However, one could expect that the spatially-averaged near-field enhancement would be much lower due to the specific pattern of the field distributions, and more important in deciding the resulting enhancement due to the nonspecific positioning of the QDs. Furthermore, it was found that due to the inherent absorption and fluorescence at visible wavelengths of most materials used in such fabrication processes results in additional loss to the resonance. In the fabricated device, the combination of the spin-on glass material (Nanoglass™, Honeywell) for the grating layer and $TiO_2$ for the high index layer was strongly absorbing and fluorescent at the excitation wavelength. This can be seen by the enhancement of the background signal from regions on the photonic crystal where no quantum dots are present (FIG. 6(b)). Indeed, the enhanced fields produced due to the resonance effect serve also to boost the background signal over 13 times, presenting a strong, undesirable loss mechanism that reduces the excitation intensity available to the QDs. Alternative fabrication methods and material choices can be used to minimize such losses, as known in the art.

For the enhanced extraction case, the fluorescence enhancement is believed to be mostly related to Bragg scattering. The structure fabricated in this example, due to its asymmetric nature, cannot posses a bandgap for either TE or TM-like modes and therefore, the effect of inhibited spontaneous emission into undetectable waveguide modes is absent. Time-resolved fluorescence measurements on the QDs both on and off the photonic crystal surface helped verify the absence of cavity enhanced spontaneous emission via the Purcell effect (data not shown). Enhanced extraction was verified by angle-resolved fluorescence measurements. By illuminating the photonic crystal and measuring the fluorescence emitted by the QDs at different angles, the enhanced extraction phenomenon was verified and shows strong coupling between the extraction modes and the QDs. The extraction effects may be further optimized by reducing the anisotropy of the in-plane wave vector, by employing photonic lattices whose Brillouin zones are more circular, e.g. triangular or quasi-periodic lattices. The density of extraction modes will also affect the extraction efficiency. A greater density of modes that overlap the emission spectrum of the QDs, would result in stronger scattering and consequently extraction effects. Finally, by engineering the spectral overlap and dispersion properties of the various leaky modes supported by the photonic crystal one can extend the enhancement effect to a wide range of fluorescent species.

Such a fluorescence enhancement scheme can be invaluable to the application of fluorescent biosensing using QDs, for example. Given the excellent applicability of QDs to serve as fluorescent probes, a highly sensitive fluorescence detection system is provided that will enable working at very low/single molecule analyte concentrations. Such a detection scheme will inherently incorporate low background fluorescence, as the QD tags close to the biosensor surface will experience maximum fluorescence enhancement, similar to total internal reflection fluorescence (TIRF) microscopy.

Here, we have demonstrated resonant enhancement of over 108 times in fluorescence from QDs on the surface of a 2D photonic crystal. This has been achieved by engineering the photonic crystal such that it possesses leaky eigenmodes (resonance mode) at the absorption and emission wavelengths of the QDs. The results of this work can be adapted to a wide variety of optical applications involving QDs, including high brightness LEDs, optical switches and high sensitivity biosensors.

Fabrication Methods

The two-dimensional photonic crystals described herein can be fabricated by a nano-replica molding process, described in the previously cited patent literature. Briefly, electron beam lithography (JEOL JBX-6000FS) was used to define a two-dimensional 'square lattice of holes' surface structure of period $\Lambda=300$ nm and hole radius $r=90$ nm on a $SiO_2/Si$ substrate with PMMA as the mask layer. The pattern was exposed to a size of $3\times3$ mm² followed by development and dry etching in a CHF3 reactive ion etching process. The resulting surface structure was subsequently transferred to a glass substrate (PET film or glass), coated with a low-index porous spin-on-glass (Nanoglass, Honeywell) using an intermediate polydimethylsiloxane (PDMS) stamp. A thin layer of high index $TiO_2$ (t=125 nm) was then sputtered (AJA International Inc.) to form the final device. The refractive indices (RI) of the Nanoglass (ng) and $TiO_2$ materials as determined by spectroscopic ellipsometry (Woolam) were $n_{ng}=1.17$ and $n_{TiO2}=2.46$ respectively at $\lambda=488$ nm.

Simulation and Device Design

A commercial implementation of the RCWA code (GSolver) was employed for all the simulations. One period of the device was simulated, with periodic boundary conditions applied to the x and y extents. The incident radiation was set to be S-polarized plane waves incident from above the device and along the $\Gamma$-M direction ($\theta=45°$, the choice of these launch parameters were essentially dictated by limitations of our experimental setup). To improve the calculation speed for the leaky mode band structure, the materials were assumed lossless and the RI dispersion was assumed to be flat about $\lambda=488$ nm. Near-field calculations however, were performed including the complex component of the material refractive indices ($k_{NG}=0$ and $k_{TiO2}=0.00036$) and retaining 12 harmonics in both the x and y directions.

NSOM Measurements of Fabricated Devices and Near-Field Enhancement.

Photonic crystal (PC) slab devices fabricated by nano-replica molding were inspected using the Witec Alpha near-field scanning microscope (NSOM). The devices were excited with $\lambda=488$ nm excitation from an argon-ion laser and the near fields were probed close to resonance. The resulting near-field intensity map is shown in FIG. 7 and shows a distribution qualitatively identical to the simulated near-field in FIG. 4(b), within the limited lateral resolution of the NSOM.

Figure 7:
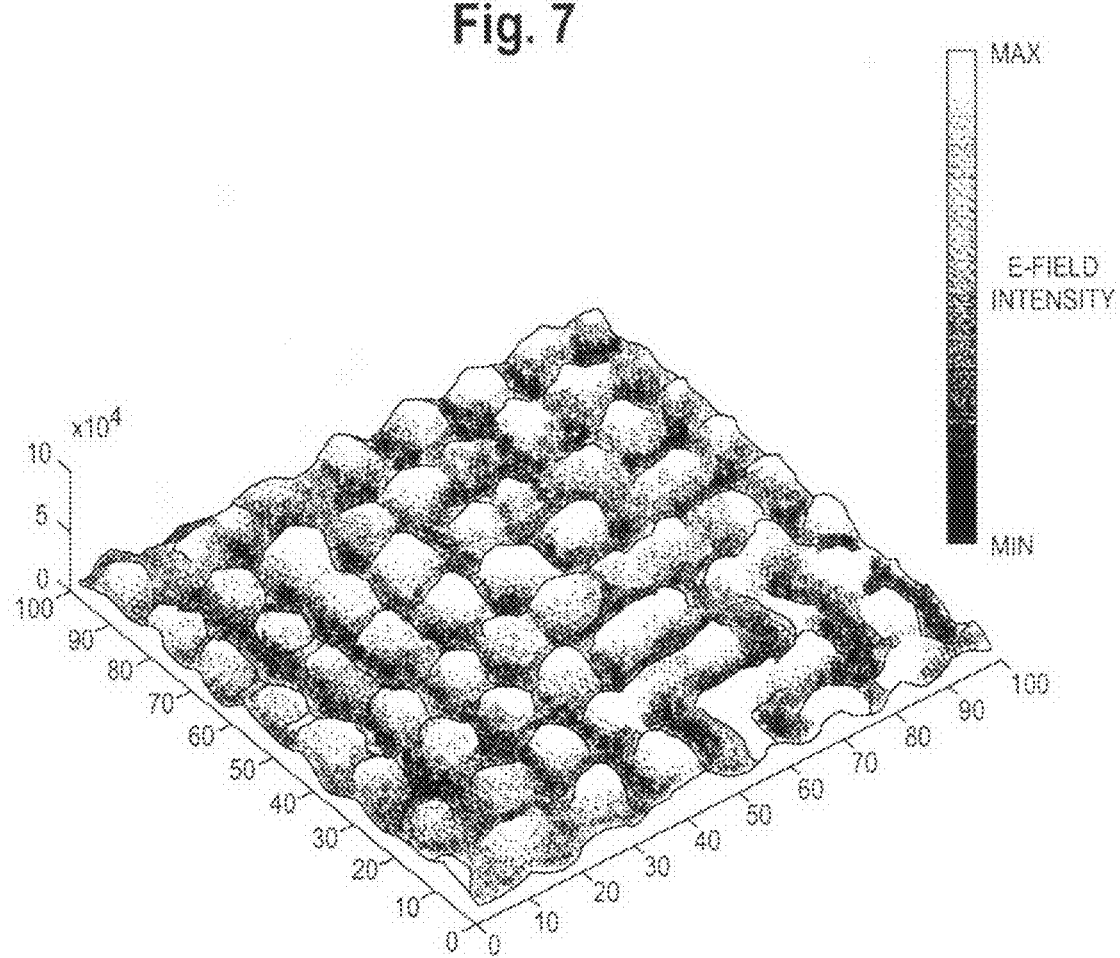
FIG. 7 is a near-field scanning optical microscopy (NSOM) image of the near-fields on the surface of a fabricated photonic crystal device.

Enhancement of the near-field is also evident in the NSOM image of FIG. 7. Defects incorporated into the device during fabrication are clearly visible as regions where the nearfield distributions are distorted.

From FIGS. 4a and 4b one can predict the absolute maximum enhancement obtainable by spatially averaging the predicted near-field distributions over the device surface. For the distributions relevant to the designed devices, a maximum average intensity of ~240 times is calculated at the device surface. However due to unavoidable resonator losses and finite size of the quantum dots (~5 nm), the practical enhancement in the excitation intensity would be lower.

Experiments Verifying the Enhanced Extraction Provided by the Photonic Crystal.

In order to verify the enhanced extraction effect of the photonic crystal due to the overlap of its leaky eigenmodes with the fluorescence spectrum of the QDs, angle-resolved fluorescence measurements were performed. The QDs were used at a 100× higher concentration (123.5 nM) for this experiment to provide sufficient signal for detection. Using a higher concentration resulted in the band structure of the leaky modes being slightly red-shifted, due to the increase in effective-index for the resonances. Consequently, this results in slightly increased angles for extraction.

The enhanced extraction phenomenon is believed to occur when the leaky modes (termed extraction modes) of the photonic crystal overlap with the QD fluorescence emission spectra. This overlap creates 'channels' into which the QDs can couple their energy. Since the modes are by definition leaky, this coupled emission from the QDs must also leak into free-space. The direction (angles) of leakage will also follow the dispersion of the extraction modes. In order to extract all the emitted light in a single direction, the bandwidth of the leaky mode to should be equal to or larger than the fluorescence bandwidth. This has been explained as the rationale behind designing photonic crystals with a relatively low Q-factor extraction modes.

In experiment, the photonic crystal containing the QDs on its surface was mounted on a fixed stage. Incident light from a $\lambda$=488 nm, 10 mW argon-ion laser was normally incident on the device, and provided the required excitation for the QDs. It must be noted that the incident light is not resonant with the photonic crystal at this angle, and therefore the near-fields are not enhanced. The fluorescence was detected from the sample by a fiber probe set at a distance of L=10 cm from the device center. A band stop filter filtered out the laser excitation so that only fluorescence from the QDs was observed. The probe was rotated about the device and the fluorescence spectrum was collected. By rotating the sample orientation, the spectrum Was recorded for both the Γ-M and Γ-X directions.

Figure 8:
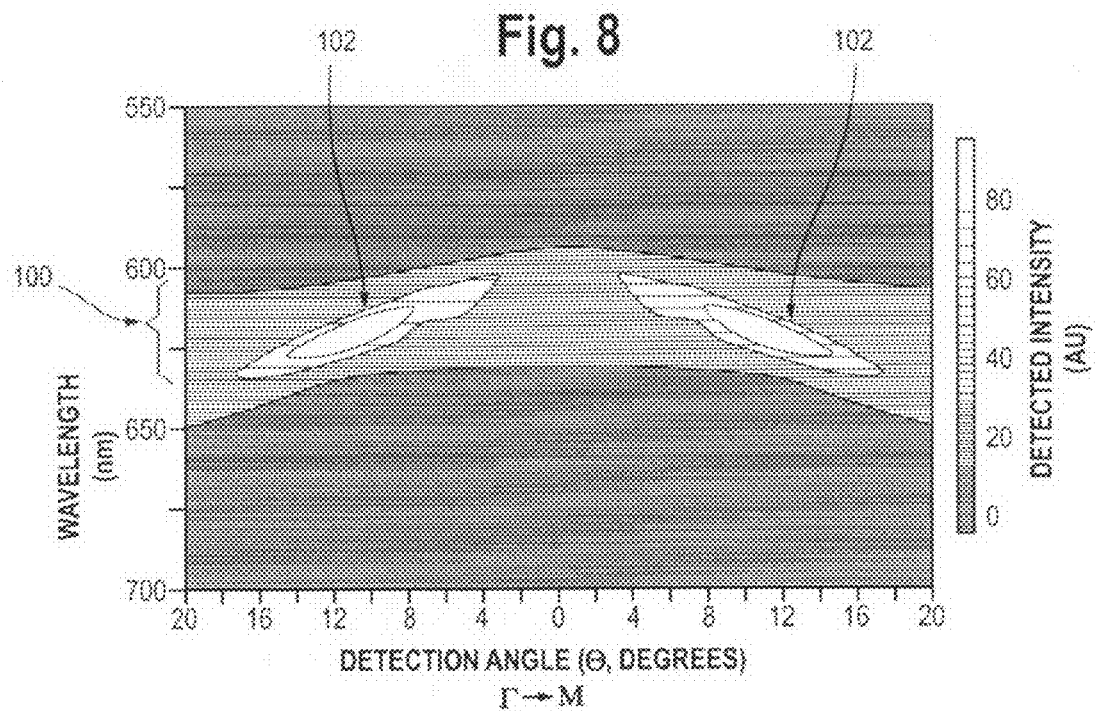
FIG. 8 is an illustration of an angle-resolved fluorescence measurement from the photonic crystal surface for the Γ-X direction.

FIG. 8 shows the angle resolved fluorescence spectrum as measured from the PC when the measurement is taken along the Γ-M direction. Since a polarizer is not used to filter the emitted radiation, all polarizations of emitted radiation are detected in the same measurement. For the case of the Γ-M direction, a broad angle-independent fluorescence feature that ranges from 600-650 nm is seen, indicated by the lighter region 100. This is the fluorescence from the QDs. Superimposed upon this feature, strong features that match the extraction mode band structure experimentally determined in FIGS. 2 & 4 are seen, indicated by the bright regions of highest detected intensity in FIG. 8, indicated at 102. This is a clear representation of the strong coupling between the QD fluorescence and the leaky modes of the PC. As seen, the fluorescence is also enhanced when the leaky modes overlap the fluorescence spectrum, the strongest enhancement being obtained when the peak of the leaky mode overlaps the peak wavelength of the fluorescence emission spectrum.

Figure 9:
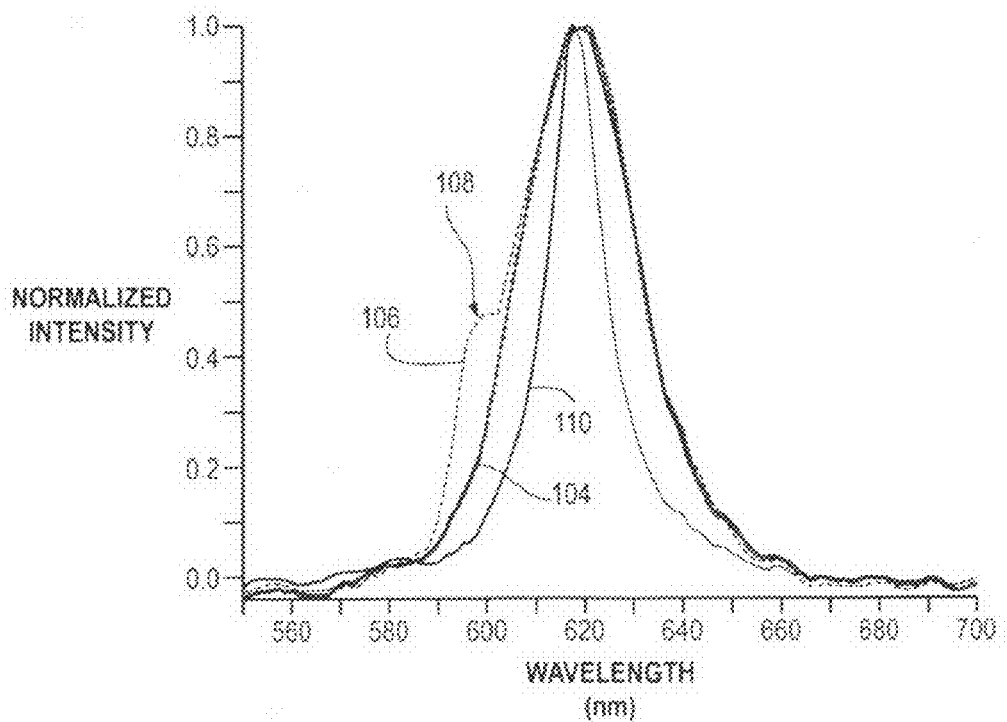
FIG. 9 is a graph of the normalized fluorescence spectrum of a quantum dot fluorescence as modified by the photonic crystal sensor.

A different way of looking at the two-dimensional experimental data shown in FIG. 8 is shown in FIG. 9, where slices of data from FIG. 8 are normalized and superimposed upon each other. In FIG. 8, the curve 104 represents the emission of the quantum dots when no photonic crystal is present. The curve 106 represents the condition when the leaky mode just begins to overlap the fluorescence spectrum of the quantum dots (at normal incidence, $\theta$=0°). A clear modification in spectral characteristics is seen, as in the appearance of a lower wavelength peak 108 resulting from enhancement of the QD sideband emission. When the peak of the emission matches the peak of the quantum dot emission (A=10°, dark square curve), a dramatic change in spectral characteristics of the emitted radiation involving emission bandwidth reducing to roughly half its original value is evident, indicated by curve 110. Thus, the presence of the photonic crystal results in strong spectral and spatial modification of the fluorescence emitted by the QDs.

Figure 10:
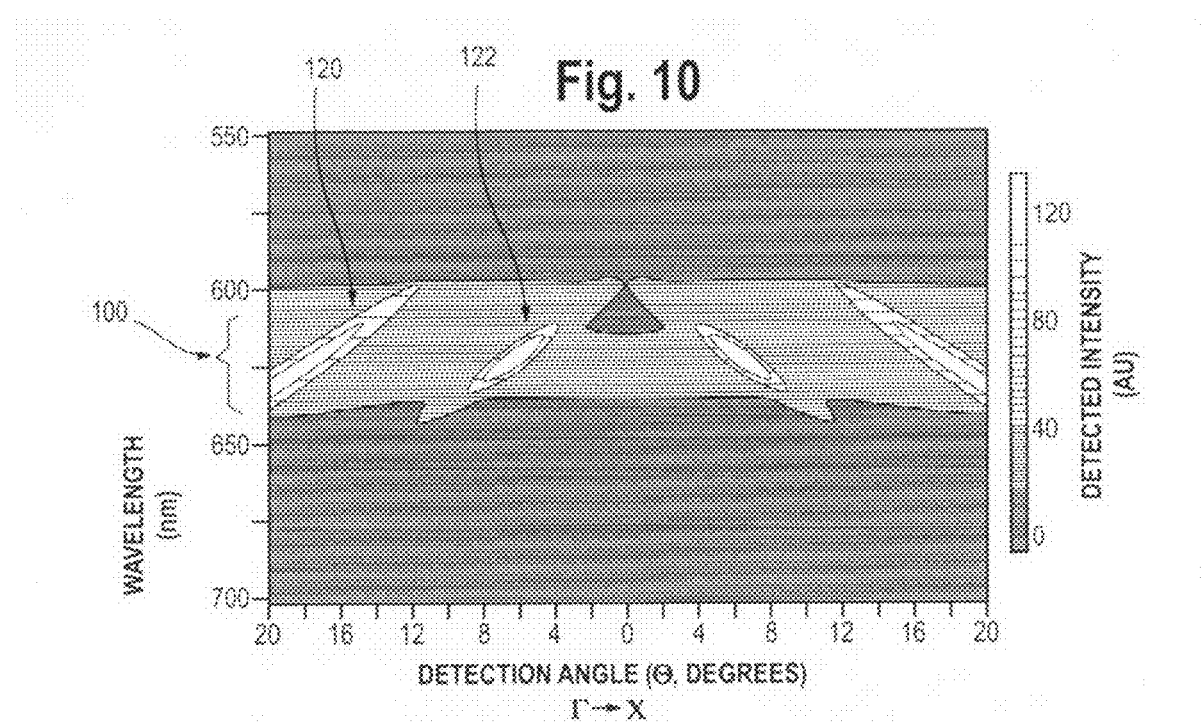
FIG. 10 illustrates angle-resolved fluorescence measurements from the photonic crystal surface for the light polarized in the Γ-M direction.

FIG. 10 shows the measurement of angle-resolved fluorescence for the Γ-X direction. In this case, two extraction bands 120 and 122 overlapping the fluorescence spectrum 100 from the QDs are seen in comparison to one as shown in FIG. 8. This is due to the fact that in the Γ-X direction, the leaky band structure for the extraction modes is different for different polarizations of coupled light. Each of the bands 120 and 122 appearing in FIG. 10 corresponds to either S-polarized or P-polarized light being emitted by the QDs. In the Γ-M direction, the dispersion of the extraction leaky modes is independent of the polarization. This is also seen clearly in FIGS. 3 & 5, where the dispersions of the extraction modes for the Γ-M direction are same for both polarizations (S & P) but different for different polarizations in the Γ-X direction.

Figure 11:
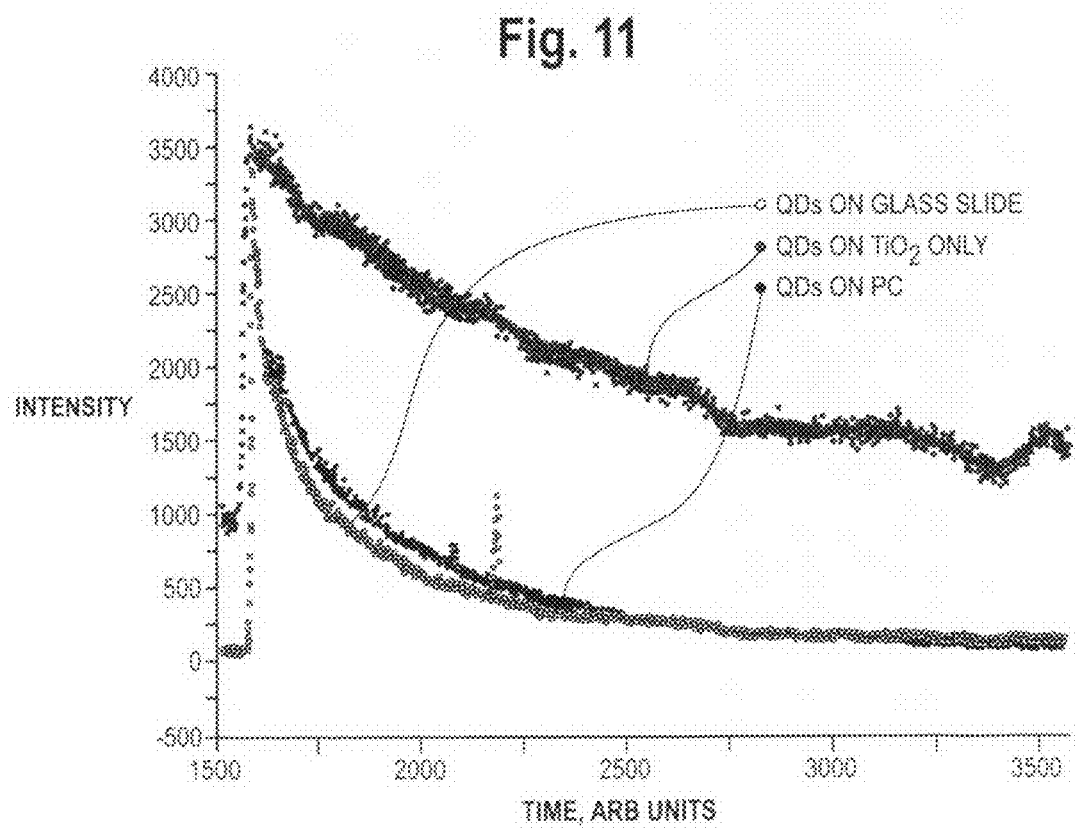
FIG. 11 is a graph of the intensity of quantum dot emission as a function of time.

FIG. 11 is a graph of the intensity of quantum dot emission as a function of time, showing that quantum dots decay significantly faster when placed on either a TiO2 substrate or a photonic crystal as compared to a glass slide.

While the above example has used a quantum dot fluorophore, the invention is applicable to detection of any fluorophore or fluorescently-labeled group. Using a non-QD fluorophore (such as an organic fluorescent dye) with the inventive photonic crystal sensor will still provide significant fluorescence sensitivity enhancement.

Extraction Mode Only Sensors

While the above example has demonstrated a photonic crystal sensor with resonance modes which overlap both the excitation and emission spectra of a fluorophore, in another embodiment the photonic crystal can be structured and arranged such that the photonic crystal exhibits a resonant mode when illuminated with light at an incident angle $\theta$ which at least partially overlaps the emission spectrum of the fluorophore, but the photonic crystal does not simultaneously have a resonance mode which overlap the excitation spectrum of the fluorophore. Such a sensor would exhibit the enhanced extraction effect but not the enhanced excitation effect. The sensor would be useful of many applications, such as those described previously.

A sample testing system for testing a sample is envisioned using a sensor featuring just the enhanced extraction mode. The system would include a detection instrument comprising a light source and a detector, and a photonic crystal sensor comprising a periodic grating structure, with the sample including the fluorophore being placed on the periodic grating structure. The light source of the detection system is oriented relative to the photonic crystal sensor such that the light source illuminates the photonic crystal sensor at a incident angle $\theta$ in which the photonic crystal exhibits a resonant mode having a resonant spectrum which at least partially overlaps the emission spectrum of the fluorophore. The detector operates to detect radiation from the fluorophore in the emission spectrum.

Yet further, in this embodiment, a method is provided for testing a sample having a fluorophore bound to the sample. The method includes the steps of placing the sample onto the surface of a photonic crystal sensor; illuminating the photonic crystal biosensor with light at an angle of incidence $\theta$, the biosensor responsively exhibiting an extraction resonance mode having a spectrum which at least partially overlaps the emission spectrum of the fluorophore, the illumination and the resulting extraction resonance mode causing the fluorophore to emit light; and collecting the emitted light from the fluorophore and directing the emitted light onto a detector.

Other Examples

Photonic Crystal Constructions

The substrate layer and grating layers of the photonic crystal sensor may be formed from inorganic materials such as glass, $SiO_2$, quartz, silicon, and of different organic and inorganic components or layers as composite materials. Alternatively the layers can be formed from organic materials such as polymers preferably polycarbonate (PC), poly (methyl methacrylate) (PMMA), polyimide (PI), polystyrene (PS), polyethylene (PE), polyethylene terepthalate (PET) or polyurethane (PU). Substrate materials also include polycarbonate or cyclo-olefin polymers such as Zeanor®.

The high index of refraction layer on the top of the substrate may be formed from inorganic materials. Examples include metal oxides such as $Ta_2O_5$, $TiO_2$, $Nb_2O_5$, $ZrO_2$, ZnO or $HfO_2$.

The embodiment of a two-dimensional grating structure suitable for simultaneous fluorescence enhancement by enhanced fluorescence excitation and enhanced extraction is disclosed and may be preferred in some implementations. A two-dimensional grating can look like a waffle (holes), a waffle iron (posts), or a chessboard configuration with alternating high and low regions in two dimensions, for example. Two-dimensional gratings can have different periods in the X and Y directions. These features may have various profiles in the Z direction such as angled or curved sidewalls. Thus, in the case of the waffle pattern, the impressions or wells may have a rectangular rather than a square shape. This added flexibility provided by two dimensional gratings allows one to tune the resonance positions for enhanced excitation and extraction detection to occur at different wavelengths. As an example, the X periodicity can provide a sharp resonance at or near normal incidence with wavelength tuned to excite the fluorophore while the Y periodicity can yield a broad resonance that coincides with the emission wavelength of the fluorophore. In one particular example, the X periodicity provides a resonance tuned to excite a Cy3 fluorophore with green light, while the Y periodicity gives a broad resonance that coincides with the emission wavelength of Cy3.

A single photonic crystal surface may be used to support, in parallel, a large number of fluorescence assays in the form of an array of probes or capture molecules that are deposited upon different locations. Each probe/capture molecule (the terms probes and capture molecules are used interchangeably herein) may contain individual and/or mixtures of capture molecules which are capable of affinity reactions. The shape of an individual capture molecule may be rectangular, circular, ellipsoidal, or any other shape. The area of an individual capture element may be any suitable area, such as between 1 $\mu m^2$ and 10 $mm^2$, between 20 $\mu m^2$ and 1 $mm^2$ and in one embodiment, between 100 $\mu m^2$ and 1 $mm^2$. The capture molecules may be arranged in a regular two dimensional array. The center-to-center (ctc) distance of the capture elements may be any suitable distance, such as between 1 $\mu m$ and 1 mm, between 5 $\mu m$ to 1 mm, and between 10 $\mu m$ to 1 mm.

The number of capture elements per sensing region is between 1 and 1,000,000, preferably between 1 and 100,000. In another aspect, the number of capture elements to be immobilized on the platform may not be limited and may correspond to the number of desired features under investigation e.g. the number of genes, DNA sequences, DNA motifs, DNA micro satellites, single nucleotide polymorphisms (SNPs), proteins or cell fragments constituting a genome of a species or organism of interest, or a selection or combination thereof. In a further aspect, the platform of this invention may contain the genomes of two or more species, e.g. mouse and rat, or human and mouse.

Sensor Platforms

The photonic crystal structures of this disclosure may be produced uniformly over large surface areas using a nanoreplica molding process. After manufacture, the structure may be incorporated onto the surface of microscope slides, within standard format microplates, or any other convenient assay format, including microarray formats. A microarray format typically includes a large number (e.g., 10,000, or 100,000) of distinct locations. Such locations are typically laid out in a regular grid pattern in x-y coordinates. However, a microarray can be laid out in any type of regular or irregular pattern. For example, distinct locations can define a microarray of spots of one or more specific binding substances. A microarray spot can be about 50 to about 500 $\mu m$ in diameter or any other suitable diameter. A microarray on a support to be used in this invention can be used by placing microdroplets of a sample including one or more specific binding substances and fluorophores onto, for example, an xy grid of locations on a two-dimensional grating or cover layer surface. When the biosensor is exposed to a test sample comprising one or more binding partners, the binding partners will be preferentially attracted to distinct locations on the microarray that comprise specific binding substances that have high affinity for the binding partners. Some of the distinct locations will gather binding partners onto their surface, while other locations will not.

One example of a microarray to be used in a method according to the present invention is a nucleic acid microarray, in which each distinct location within the array contains a different nucleic acid molecule. In this embodiment, the spots within the nucleic acid microarray detect complementary chemical binding with an opposing strand of a nucleic acid in a test sample.

The sensors described here can be used to sensitively analyze a variety of analytes. Some examples of analytes that can be detected using the sensors and methods herein include, but are not limited to, one or more: proteins, peptides, DNA molecules, RNA molecules, oligonucleotides, lipids, carbohydrates, polysaccharides; glycoproteins, lipoproteins, sugars, cells, bacteria, viruses, candidate molecules and all derivatives, variants and complexes of these, which have a fluorescent label. Other fluorescent substances can be detected, as known in the art. Nanomaterials such as quantum dots or functionalized quantum dots may be used. Applications include gene expression microassays where genes may be detected at lower expression levels and/or with Y smaller sample volumes. Other applications include protein detection assays, such as detection of protein biomarkers in bodily fluids for disease diagnostic tests, where proteins are present at very low concentration. Detection by the method described in this invention would be more sensitive than commonly used ELISA assays, but with a simpler assay protocol. In addition, fluorescent imaging of cells and proteins using fluorescent microscopes can utilize the techniques presented here, where the improved sensitivity can be used to observe dye molecules at lower concentrations and/or to use lower-cost imaging came due to improved signal-to-noise ratio Alternative Grating Structures In one embodiment, a support to be used in a method of the invention will be illuminated with white light that will contain light of every polarization angle. The orientation of the polarization angle with respect to repeating features in a biosensor grating will determine the resonance wavelength. For example, a "linear grating" biosensor structure consisting of a set of repeating lines and spaces will have two optical polarizations that can generate separate resonant reflections. Light that is polarized perpendicularly to the lines is called "s-polarized," while light that is polarized parallel to the lines is called "p-polarized." Both the s and p components of incident light exist simultaneously in an unfiltered illumination beam, and each generates a separate resonant signal. A support structure can generally be designed to optimize the properties of only one polarization (the s-polarization), and the non-optimized polarization is easily removed by a polarizing filter.

In order to remove the polarization dependence, so that every polarization angle generates the same resonant reflection spectra, an alternate structure can be used that consists of a set of concentric rings. In this structure, the difference between the inside diameter and the outside diameter of each concentric ring is equal to about one-half of a grating period. Each successive ring has an inside diameter that is about one grating period greater than the inside diameter of the previous ring. The concentric ring pattern extends to cover a single sensor location—such as a microarray spot or a microtitre plate well. Each separate microarray spot or microtitre plate well has a separate concentric ring pattern centered within it. All polarization directions of such a structure have the same cross-sectional profile. The concentric ring structure must be illuminated precisely on-center to preserve polarization independence. The grating period of a concentric ring structure is less than the wavelength of the resonantly reflected light. The grating period is about 0.01 micron to about 1 micron, in one embodiment. The grating depth is about 0.01 to about 1 micron, in one embodiment.

In another embodiment, an array of holes or posts are arranged to closely approximate the concentric circle structure described above without requiring the illumination beam to be centered upon any particular location of the grid. Such an array pattern is automatically generated by the optical interference of three laser beams incident on a surface from three directions at equal angles. In this pattern, the holes (or posts) are centered upon the corners of an array of closely packed hexagons. The holes or posts also occur in the centre of each hexagon. Such a hexagonal grid of holes or posts has three polarization directions that "see" the same cross-sectional profile. The hexagonal grid structure, therefore, provides equivalent resonant reflection spectra using light of any polarization angle. Thus, no polarizing filter is required to remove unwanted reflected signal components. The period of the holes or posts can be about 0.01 μm to about 1 μm and the depth or height can be about 0.01 μm to about 1 μm.

The detecting system may be arranged to detect luminescence such as fluorescence. Affinity partners can be labeled in such a way that Förster fluorescence energy transfer (FRET) can occur upon binding of analyte molecules to capture molecules. The maximum of the luminesce labels can be used to modify capture elements, assayed molecules in the analyte, or any other species, e.g. endogeneous/exogeneous controls, spacer molecules, primers, bio/materials, that interact with the sensor surface.

The luminescence dyes used as markers may be chemically or physically, for instance electrostatically, bonded to one or multiple affinity binding partners (or derivatives thereof) present in the analyte solution and/or attached to the platform. In case of naturally occurring oligomers or polymers such as DNA, RNA, saccharides, proteins, or peptides, as well as synthetic oligomers or polymers, involved in the affinity reaction, intercalating dyes are also suitable. Luminophores may be attached to affinity partners present in the analyte solution via biological interaction such as biotin/avidin binding or metal complex formation such as HIStag coupling.

One or multiple luminescence markers may be attached to affinity partners present in the analyte solution, to capture elements immobilized on the platform, or both to affinity partners present in analyte solution and capture elements immobilized at the platform, in order to quantitatively determine the presence of one or multiple affinity binding partners.

The samples may be used either undiluted or with added solvents. Suitable solvents include water, aqueous buffer solutions, protein solutions, natural or artificial oligomer or polymer solutions, and organic solvents. Suitable organic solvents include alcohols, ketones, esters, aliphatic hydrocarbons, aldehydes, acetonitrile or nitriles.

Solubilisers or additives may be included, and may be organic or inorganic compounds or biochemical reagents such as diethylpyrocarbonate, phenol, formamide, SSC (sodium citrate/sodium chloride), SDS (Sodiumdodecylsulfate), buffer reagents, enzymes, reverse transcriptase, RNAase, organic or inorganic polymers.

Fluorophores and Fluorescent Labels

While the above examples have used quantum dots as the fluorescent molecule which is excited by incident radiation, other fluorophores can be used in accordance with the inventive biosensor.

Transfluorospheres or derivatives thereof may be used for fluorescence labeling, and chemiluminescent or electroluminescent molecules may be used as markers.

Luminescent compounds having luminescence in the range of from 400 nm to 1200 nm which are functionalised or modified in order to be attached to one or more of the affinity partners may be used, including derivatives of: polyphenyl and heteroaromatic compounds, stilbenes, coumarines, xanthene dyes, methine dyes, oxazine dyes, rhodamines, fluoresceins, coumarines, stilbenes, pyrenes, perylenes, cyanines, oxacyanines, phthalocyanines, porphyrines, naphthalopcyanines, azobenzene derivatives, distyryl biphenyls, transition metal complexes e.g. polypyridyl/ruthenium complexes, tris (2,2' bipyridyl) ruthenium chloride, tris(1,10-phenanthroline) ruthenium chloride, tris (4,7 diphenyl-1,10-phenanthroline) ruthenium chloride and polypyridyl/phenazine/ruthenium complexes, such as octaethyl-platinum-porphyrin, Europium and Terbium complexes may be used as luminescence markers, nanoparticles, microparticles, or any other light emitting species that can be excited by evanescent fields.

Suitable for analysis of blood or serum are dyes having absorption and emission wavelength in the range from 400 nm to 1000 nm. Furthermore luminophores suitable for two and three photon excitation can be used.

Dyes which are suitable in this invention may contain functional groups for covalent bonding, e.g. fluorescein derivatives such as fluorescein isothiocyanate. Also suitable are the functional fluorescent dyes commercially available from Amersham Life Science, Inc., Texas, and Molecular Probes Inc. Other suitable dyes include dyes modified with deoxynucleotide triphosphate (dNTP) which can be enzymatically incorporated into RNA or DNA strands. Further suitable dyes include Quantum Dot Particles or Beads (Quantum Dot Cooperation, Palo Alto, Calif.) or derivatives thereof or derivatives of transition metal complexes which may be excited at one and the same defined wavelength, and derivatives show luminescence emission at distinguishable wavelengths.

Analytes may be detected either via directly bonded luminescence markers, or indirectly by competition with added luminescence marked species, or by concentration, distance, pH, potential- or redox potential-dependent interaction of luminescence donors and luminescence/electron acceptors used as markers bonded to one and/or multiple analyte species and/or capture elements. The luminescence of the donor and/or the luminescence of the quencher can be measured for the quantification of the analytes.

In the same manner affinity partners can be labeled in such a way that electron transfer or photoinduced electron transfer leads to quenching of fluorescence upon binding of analyte molecules to capture molecules.

Luminescent labels can be used to modify capture elements, assayed molecules in the analyte, or any other species, e.g. endogeneous/exogeneous controls, spacer molecules, primers, bio/materials, that interact with the sensor surface.

The luminescence dyes used as markers may be chemically or physically, for instance electrostatically, bonded to one or multiple affinity binding partners (or derivatives thereof) present in the analyte solution and/or attached to the platform. In case of naturally occurring oligomers or polymers such as DNA, RNA, saccharides, proteins, or peptides, as well as synthetic oligomers or polymers, involved in the affinity reaction, intercalating dyes are also suitable. Luminophores may be attached to affinity partners present in the analyte solution via biological interaction such as biotin/avidin binding or metal complex formation such as HIStag coupling.

One or multiple luminescence markers may be attached to affinity partners present in the analyte solution, to capture elements immobilized on the platform, or both to affinity partners present in analyte solution and capture elements immobilized at the platform, in order to quantitatively determine the presence of one or multiple affinity binding partners.

Capture Molecules Bound to Fluorophores

The fluorophores described herein (e.g., quantum dots) are functionalized by being bound to capture molecules which are in turn deposited onto the surface of the photonic crystal biosensor. The nature of the capture molecules are many and varied. Generally speaking the capture molecules used should be capable of affinity reactions. Examples of capture molecules which can be used in the context of this invention include: nucleotides, oligonucleotides (and chemical derivatives thereof) DNA (double strand or single strand) a) linear (and chemical derivatives thereof) b) circular (e.g. plasmids, cosmids, BACs, ACs), total RNA, messenger RNA, cRNA, mitochondrial RNA, artificial RNA, aptamers, PNA (peptide-nucleic acids) Polyclonal, Monoclonal, recombinant, engineered antibodies, antigenes, haptens, antibody FAB subunits (modified if necessary), proteins, modified proteins, enzymes, enzyme cofactors or inhibitors, protein complexes, lectines, Histidine labeled proteins, chelators for Histidinetag components (HIStag), tagged proteins, artificial antibodies, molecular imprints, plastibodies, membrane receptors, whole cells, cell fragments and cellular substructures, synapses, agonists/antagonists, cells, cell organelles, e.g. microsomes, small molecules such as benzodiazapines, prostaglandins, antibiotics, drugs, metabolites, drug metabolites, natural products, carbohydrates and derivatives, natural and artificial ligands, steroids, hormones, peptides, native or artificial polymers, molecular probes, natural and artificial receptors and chemical derivatives thereof, chelating reagents, crown ether, ligands, supramolecular assemblies, indicators (pH, potential, membrane potential, redox potential), viruses, bacteria and a tissue sample from an animal or plant subject.

In biological applications, the sample can be for example, blood, plasma, serum, gastrointestinal secretions, homogenates of tissues or tumors, synovial fluid, feces, saliva, sputum, cyst fluid, amniotic fluid, cerebrospinal fluid, peritoneal fluid, lung lavage fluid, semen, lymphatic fluid, tears, or prostatic fluid.

The biosensor surface may include an adhesion promoting layer disposed at the surface of the optically transparent layer (high index of refraction layer) in order to enable immobilization of capture molecules. The adhesion promoting layer may also comprise a microporous layer (for example, ceramics, glass, Si) for further increasing assay and detection efficacy or of gel layers which either can be used as medium for carrying out the capture element immobilization and sample analysis, thereby further increasing the assay and detection efficacy, or which allow separation of analyte mixtures in the sense of gel electrophoresis. The platform may be formed with a plurality of sensing areas or regions, each having its own diffractive grooves.

In other words, immobilization of one or more probes/capture molecules onto a biosensor surface can be performed so that a specific binding substance will not be washed away by rinsing procedures, and so that its binding to binding partners in a test sample is unimpeded by the biosensor surface. Several different types of surface chemistry strategies have been implemented for covalent attachment of specific binding substances to, for example, glass for use in various types of microarrays and biosensors. These same methods can be readily adapted to a biosensor of the invention. Surface preparation of a biosensor so that it contains the correct functional groups for binding one or more specific binding substances is an integral part of the biosensor manufacturing process.

One or more specific binding substances can hence be attached to a biosensor surface by physical adsorption (i.e., without the use of chemical linkers) or by chemical binding (i.e., with the use of chemical linkers). Chemical binding can generate stronger attachment of specific binding substances on biosensor surface and provide defined orientation and conformation of the surface-bound molecules. For instance, some types of chemical binding include, for example, amine activation, aldehyde activation, and nickel activation. These surfaces can be used to attach several different types of chemical linkers to a biosensor surface. While an amine surface can be used to attach several types of linker molecules, an aldehyde surface can be used to bind proteins directly, without an additional linker. A nickel surface can be used to bind molecules that have an incorporated histidine ("his") tag. Detection of "his-tagged" molecules with a nickel-activated surface is well known in the art (Whitesides, *Anal. Chem.* 68, 490 (1996)).

Immobilization of specific binding substances to plastic, epoxy, or high refractive index material can be performed similarly to that described for immobilization to glass. However, the acid wash step can be eliminated where such a treatment would damage the material to which the specific binding substances are immobilized. This is well known in the art.

For the detection of binding partners at concentrations less than about 0.1 ng/ml, it is possible to amplify and transduce binding partners bound to a biosensor into an additional layer on the biosensor surface. The increased mass deposited on the biosensor can be easily detected as a consequence of increased optical path length. By incorporating greater mass onto a biosensor surface, the optical density of binding partners on the surface is also increased, thus rendering a greater resonant wavelength shift than would occur without the added mass. The addition of mass can be accomplished, for example, enzymatically, through a "sandwich" assay, or by direct application of mass to the biosensor surface in the form of appropriately conjugated beads or polymers of various size and composition. This principle has been exploited for other types of optical biosensors to demonstrate sensitivity increases over 1500 beyond sensitivity limits achieved without mass amplification. See, e.g., Jenison et al., "Interference-based detection of nucleic acid targets on optically coated silicon," *Nature Biotechnology* 19: 6265 (2001).

As an example, a $NH^2$-activated biosensor surface can have a specific binding substance comprising a single-strand DNA capture probe immobilized on the surface.

The capture probe interacts selectively with its complementary target binding partner. The binding partner, in turn, can be designed to include a sequence or tag that will bind a "detector" molecule. A detector molecule can contain, for example, a linker to horseradish peroxidase (HRP) that, when exposed to the correct enzyme, will selectively deposit additional material on the biosensor only where the detector molecule is present. Such a procedure can add, for example, 300 angstroms of detectable biomaterial to the biosensor within a few minutes.

A "sandwich" approach can also be used to enhance detection sensitivity. In this approach, a large molecular weight molecule can be used to amplify the presence of a low molecular weight molecule. For example, a binding partner with a molecular weight of, for example, about 0.1 kDa to about 20 kDa, can be tagged with, for example, succinimidyl6 [amethyla(2pyridyldithio) toluamido] hexanoate (SMPT), or dimethylpimelimidate (DMP), histidine, or a biotin molecule.

Detection Apparatus

The photonic crystal biosensors of this disclosure are used in conjunction with an appropriate detection apparatus or instrument. The particular nature and construction of the detection apparatus is not especially important. The detection apparatus detects the luminescent response of the fluorophores bound to a sample when the sample and fluorophore are deposited on the surface of the biosensor and the sensor is illuminated with light at a frequency which overlaps the excitation spectrum of the fluorophore. Examples of appropriate detectors for luminescence include CCD-cameras, photomultiplier tubes, avalanche photodiodes, photodiodes, hybrid photomultiplier tubes, or arrays thereof. The disclosure of the detection apparatus described in U.S. patent application publications U.S. 2003/0027327; 2002/0127565, 2003/0059855 and 2003/0032039, U.S. Pat. Nos. 7,023,544, 7,064,844, and published PCT application WO 2007/0179024, the contents of each of which is hereby incorporated herein by reference. Since the detection apparatus is described in the literature, a further explanation is omitted here for the sake of brevity. The detection apparatus can be arranged to detect in addition changes in the refractive index due to the coupling of the sample and fluorophore to the sensor surface and resulting shift in the peak wavelength of reflected light. The incident beam may be arranged to illuminate the sensing area or all sensing areas on one common platform. Alternatively the beam can be arranged to illuminate only a small subarea of the sensing area to be analyzed and the beam and/or the platform may be arranged so that they can undergo relative movement in order to scan the sensing area of the platform. Accordingly, the detecting apparatus may be arranged in an appropriate way to acquire the luminescence signal intensities of the entire sensing area in a single exposure step. Alternatively the detection and/or excitation means may be arranged in order to scan the sensing areas stepwise.

The detection instrument includes a light generating unit which illuminates the photonic crystal sensor. The light generating unit may comprise a laser emitting a coherent laser beam. Other suitable light sources include discharge lamps or low pressure lamps, e.g. Hg or Xe, where the emitted spectral lines have sufficient coherence length, and light-emitting diodes (LED). The apparatus may also include optical elements for directing the laser beam so that it is incident on the platform at an angle θ, and elements for shaping the plane of polarization of the coherent beam, e.g. adapted to transmit linearly polarized light.

Examples of lasers that may be used are gas lasers, solid state lasers, dye lasers, semiconductor lasers. If necessary, the emission wavelength can be doubled by means of nonlinear optical elements. Especially suitable lasers are argon ion lasers, krypton ion lasers, argon/krypton ion lasers, and helium/neon lasers which emit at wavelengths between 275 and 753 nm. Very suitable are diode lasers or frequency doubled diode lasers of semiconductor material which have small dimensions and low power consumption.

Another appropriate type of excitation makes use of VCSEL's (vertical cavity surface emitting lasers) which may individually excite the recognition elements on the platform.

In an embodiment in which the photonic crystal is incorporated onto a microscope slide, the detection instrument may include a microscope for viewing the slide. The microscope may direct a magnified image of the field of view onto an imaging device such as a charge coupled device camera which then captures and stores images of the field of view. Workstations incorporating microscopes and cameras are described in the patent literature and therefore a detailed discussion of the features of such as system are omitted for the sake of brevity.

Figure 12:
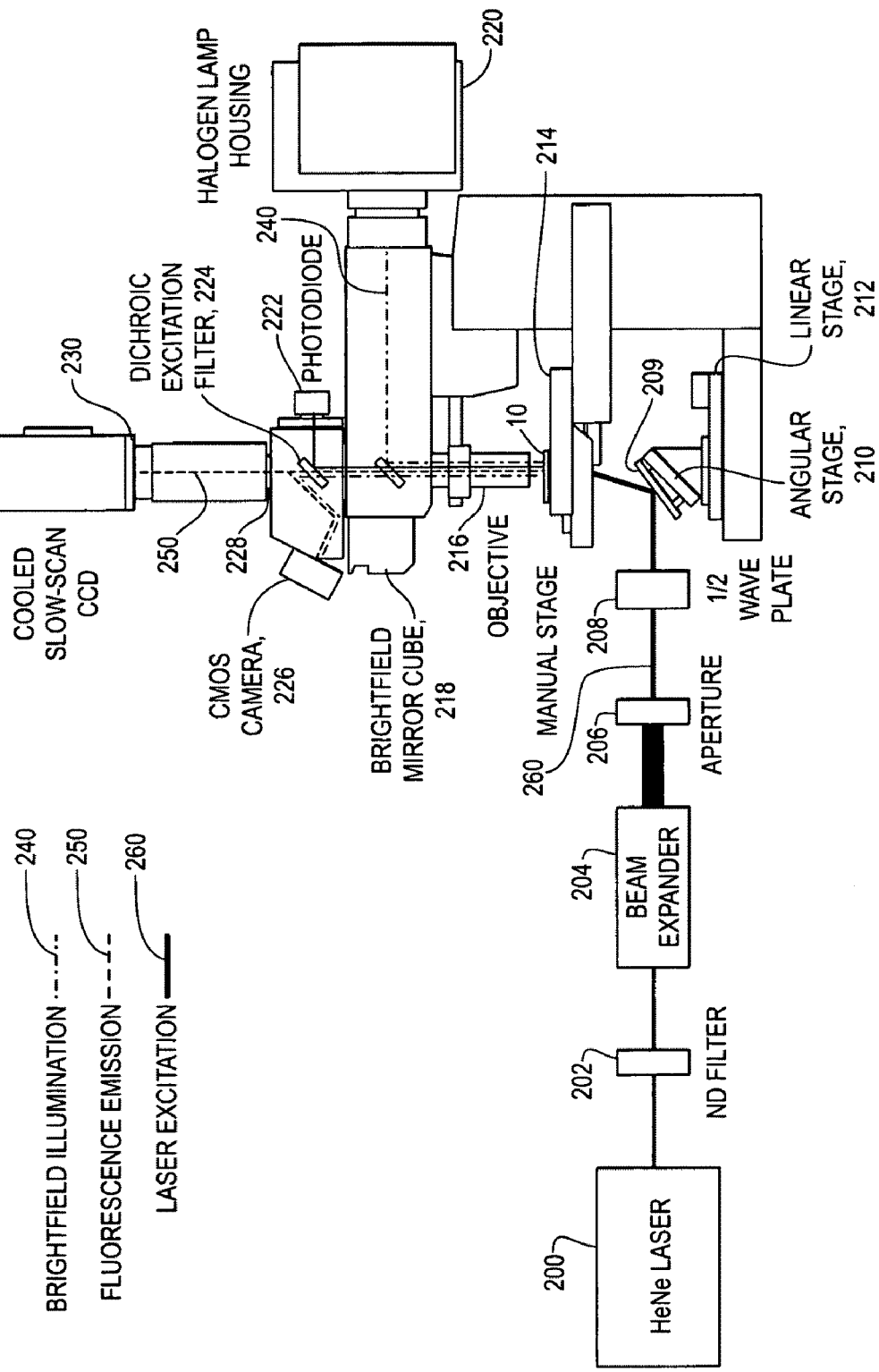
FIG. 12 is a block diagram of a detection instrument for a photonic crystal sensor featuring enhanced excitation and enhanced extraction.

FIG. 12 is block diagram of one possible embodiment of a detection instrument 190 for use with photonic crystal sensor 10 featuring enhanced excitation and enhanced extraction. The instrument 190 features a modified upright fluorescence microscope 195. The instrument 190 includes a HeNe laser 200 which directs light 260 through a neutral density filter 202 and a beam expander 204. The expanded beam is directed through an aperture 206 and a ½ wave plate 208 for polarization and onto a motorized stage of the microscope 195. The motorized stage includes a linear stage 212 for travel in the X and Y directions. An adjustable angular stage 210 is mounted to the linear stage 212 and is used to adjust the beam angle θ. Laser light from the stage is directed via a mirror 209 upwards to a manual stage 214 of the microscope 195. The photonic crystal sensor 10 (e.g., incorporated into a microscope slide) is placed on the manual stage 214. The laser excitation light 260 is tuned to match the excitation band of a fluorophore present in the sample placed on the sensor 10 and causes the fluorophore to emit fluorescence (shown by line 250).

The combination of components 200, 202, 204, 206, 208, 210 and 212 provide for an angle-tunable, beam-expanded excitation laser input. The laser beam 260 is expanded in the beam expander 204 to ensure uniform excitation across the sensor 10 and maximum collimation, and cropped with an aperture 206 to prevent photobleaching outside the imaging area. Alignment of the laser beam to the sensor 10 is achieved using a set of mirrors (one which is mounted on a precision linear stage 212), polarization is adjusted with a half-wave plate 208, and attenuated with a continuously variable neutral density filter 202. The beam is then reflected off a gimbal-mounted mirror 209 and incident upon the sensor 10. The gimbal mount is controlled with a high precision motor and is itself mounted on a linear stage 212 that also employs a high-precision motorized drive. This linear stage 212 ensures the illumination area on the sensor 10 remains fixed as the excitation beam angle θ is changed.

A halogen lamp housing 220 provides brightfield illumination for the sample placed on the sensor 10. The lamp housing 200 directs white light to a mirror cube 218 and the light is directed through the objective lens 216 of the microscope and onto the sensor 10. Magnified, brightfield images of the sample are captured by a simple CMOS camera 226.

The CMOS camera 226 allows sample focusing and low-resolution image capture.

While the variable-angle laser setup of FIG. 12 serves to maximize the enhanced excitation effect of the device, several other design elements are provided to optimize the enhanced extraction behavior. In particular, since the light-emitters on the device (fluorophores, e.g. quantum dots or organic fluorophores) couple more strongly to the resonant extraction modes than do autofluorescing materials within the device itself, attempting to exclude all light except these extraction modes provides maximum signal-to-noise for the output fluorescence. In order to accomplish this, there needs to be spatial, frequency, and polarization filtering. Spatial filtering is accomplished using a low numerical-aperture (NA) lens 216. While this constrains the extraction modes to exist within narrow angles of the normal, it provides good spatial exclusion while still enabling imaging without scanning optics. (Recall the discussion of FIG. 1 and the strongly directional nature of the enhanced extraction effect within small angles of vertical). Upstream magnification (not shown) is employed to overcome the resolution limitations of imaging with a low-NA lens. Frequency selection is done with a narrow-linewidth bandpass filter (228) that coincides with the extraction resonance linewidth. Selecting the polarization for the resonant light extraction provides further signal-to-noise improvements.

The fluorescence microscope 195 employs a dichroic mirror in conjunction with the filter 224 that reflects the excitation laser light towards a photodiode detector 222 for purposes of measuring the photonic dispersion of the sensor 10 under test.

An emission filter 228, as described previously, is used to further filter the incident fluorescence emission. This filtered output is fed to a cooled back-thinned electron-multiplier CCD (BT-EM-CCD) 230. This camera 230 has a very large dynamic range to enable high-enhancement measurements, and also has excellent sensitivity for pursuing single-molecule fluorescence detection.

While presently preferred embodiments have been described with particularly, variation from the specifics of the disclosed embodiments are of course possible without departure from the scope of the invention. All questions concerning scope are to be determined by reference to the appended claims.

We claim:

1. A detection instrument for a biosensor, comprising:
   an optical system directing light onto the biosensor comprising a laser light unit, a beam expander expanding a beam generated by the laser light unit, and a device for adjusting polarization of the light generated by the laser light unit;
   an angle-tunable mirror receiving beam-expanded laser light and directing the expanded beam to the biosensor; and
   an imaging system receiving light from biosensor, the imaging system comprising an optical path containing an objective lens, a narrow-linewidth bandpass filter and a camera;
   wherein the objective lens comprises the objective lens of a microscope and wherein the biosensor is in the form of a photonic crystal formed in a microscope slide.

2. The detection instrument of claim 1, wherein the angle-tunable mirror is mounted to a motorized stage.

3. The detection instrument of claim 1, wherein the wavelength of the laser light unit is tuned to match the excitation band of a fluorophore present in a sample placed on the biosensor.

4. The detection instrument of claim 3, wherein the frequency of the bandpass filter coincides with a resonance frequency exhibited by the biosensor.

5. The detection instrument of claim 1, wherein the camera comprises a CCD imaging camera.

6. The detection instrument of claim 1, further comprising a variable neutral density filter in the optical system directing light onto the biosensor attenuating the output of the laser light unit.

7. A detection instrument for a biosensor, comprising:
   an optical system directing light onto the biosensor comprising a laser light unit, a beam expander expanding a beam generated by the laser light unit, and a device for adjusting polarization of the light generated by the laser light unit;
   an angle-tunable mirror receiving beam-expanded laser light and directing the expanded beam to the biosensor;
   an imaging system receiving light from biosensor, the imaging system comprising an optical path containing an objective lens, a narrow-linewidth bandpass filter and a camera;
   a brightfield illumination source for illuminating the biosensor, and a second camera capturing magnified brightfield images of the biosensor.

8. The detection instrument of claim 1, further comprising a low numerical aperture lens in the optical system directing light onto the biosensor, wherein the tunable mirror receives light from the low numerical aperture lens.

9. A detection instrument for a biosensor, comprising:
   an optical system directing light onto the biosensor comprising a laser light unit, a beam expander expanding a beam generated by the laser light unit, and a device for adjusting polarization of the light generated by the laser light unit;
   an angle-tunable mirror receiving beam-expanded laser light and directing the expanded beam to the biosensor; and
   an imaging system receiving light from biosensor, the imaging system comprising an optical path containing an objective lens, a narrow-linewidth bandpass filter and a camera;
   a dichroic mirror reflecting laser light passing through the biosensor and a photodiode detector receiving the reflected laser light.

10. The instrument of claim 9, wherein the biosensor in is the form of a microwell plate having a plurality of wells, the wells having a photonic crystal sensor formed therein.

11. The instrument of claim 1, wherein the angle-tunable mirror is moved such that the camera captures an image of the biosensor at an angle of minimum transmission.

12. The instrument of claim 1, wherein the biosensor comprises a photonic crystal and, wherein a sample containing a fluorophore is applied to the biosensor, and wherein the light from the biosensor comprises enhanced fluorescence from the fluorophore, the fluorophore excited by the light from the laser light unit.

13. A detection system for a biosensor comprising a photonic crystal incorporated into a microscope slide, combining in combination a microscope and the detection instrument of claim 1.

14. A detection instrument for a photonic crystal biosensor exhibiting an enhanced excitation and extraction modes, comprising:

a laser light source;

an optical system directing light from the laser light source to the photonic crystal biosensor, the biosensor responsively and simultaneously exhibiting (1) an excitation resonance mode having a spectrum which at least partially overlaps an excitation spectrum of a fluorophore bound to the biosensor; and (2) an extraction resonance mode having a spectrum which at least partially overlaps the emission spectrum of the fluorophore, and a detection system placed to capture light from the biosensor in the extraction resonance mode.

15. The instrument of claim 14, wherein the detection system includes a camera generating an image of the biosensor.

16. The detection instrument of claim 7, further comprising a low numerical aperture lens in the optical system directing light onto the biosensor, wherein the tunable mirror receives light from the low numerical aperture lens.

17. The detection instrument of claim 7 further comprising a dichoric mirror reflecting laser light passing through the biosensor and a photodiode detector receiving the reflected laser light.

18. The instrument of claim 7, wherein the biosensor in is the form of a microwell plate having a plurality of wells, the wells having a photonic crystal sensor formed therein.

19. The instrument of claim 7, wherein the angle-tunable mirror is moved such that the camera captures an image of the biosensor at an angle of minimum transmission.

20. The detection instrument of claim 7, wherein the wavelength of the laser light unit is tuned to match the excitation band of a fluorophore present in a sample placed on the biosensor.

21. The detection instrument of claim 20, wherein the frequency of the bandpass filter coincides with a resonance frequency exhibited by the biosensor.

22. The instrument of claim 9, wherein the biosensor in is the form of a microwell plate having a plurality of wells, the wells having a photonic crystal sensor formed therein.

23. The instrument of claim 9, wherein the biosensor comprises a photonic crystal and wherein a sample containing a fluorophore is applied to the biosensor, and wherein the light from the biosensor comprises enhanced fluorescence from the fluorophore, the fluorophore excited by the light from the laser light unit.

* * * * *